United States Patent
Predick

(10) Patent No.: US 10,532,197 B2
(45) Date of Patent: Jan. 14, 2020

(54) DIRECTIONAL SEQUENTIAL DILATION SYSTEM WITH NEURO MONITORING

(71) Applicant: Life Spine, Inc., Huntley, IL (US)

(72) Inventor: Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 438 days.

(21) Appl. No.: 15/284,250

(22) Filed: Oct. 3, 2016

(65) Prior Publication Data

US 2017/0021147 A1 Jan. 26, 2017

Related U.S. Application Data

(63) Continuation-in-part of application No. 14/135,238, filed on Dec. 19, 2013, now Pat. No. 9,456,846.

(60) Provisional application No. 61/739,137, filed on Dec. 19, 2012.

(51) Int. Cl.
*A61M 29/00* (2006.01)
*A61B 17/02* (2006.01)
*A61B 17/34* (2006.01)
*A61B 17/00* (2006.01)
*A61B 5/04* (2006.01)
*A61B 5/00* (2006.01)

(52) U.S. Cl.
CPC ........... *A61M 29/00* (2013.01); *A61B 17/025* (2013.01); *A61B 17/0206* (2013.01); *A61B 17/3417* (2013.01); *A61B 17/3421* (2013.01); *A61B 5/04001* (2013.01); *A61B 5/4893* (2013.01); *A61B 2017/00039* (2013.01); *A61B 2017/00261* (2013.01); *A61B 2017/00991* (2013.01); *A61B 2017/0262* (2013.01); *A61B 2505/05* (2013.01)

(58) Field of Classification Search
CPC ............ A61B 17/3417; A61B 17/3421; A61B 17/024; A61B 17/1757; A61B 2017/3433; A61F 2/4611
See application file for complete search history.

(56) References Cited

U.S. PATENT DOCUMENTS

| | | | |
|---|---|---|---|
| 8,070,693 B2 * | 12/2011 | Ayala | A61M 25/0147 600/585 |
| 2007/0038216 A1 * | 2/2007 | Hamada | A61B 17/02 606/53 |
| 2007/0123753 A1 * | 5/2007 | Abdelgany | A61B 17/02 600/220 |
| 2011/0208226 A1 | 8/2011 | Fatone et al. | |
| 2014/0303666 A1 | 10/2014 | Heiman et al. | |

* cited by examiner

*Primary Examiner* — Diane D Yabut
(74) *Attorney, Agent, or Firm* — Foley & Lardner LLP

(57) ABSTRACT

A system for providing access to a surgical site includes a first dilator; a second dilator slidably couplable to a first side of the first dilator and including a first interface portion; a plurality of additional dilators slidably couplable to a second side of the first dilator in a nested manner; and at least one retractor member including a second interface portion removably couplable to the first interface portion. When the first interface portion is coupled to the second interface portion, and the second dilator and the plurality of additional dilators are coupled to the first dilator, the second dilator and the at least one retractor member form a retractor wall extending about the first dilator and the plurality of additional dilators.

14 Claims, 22 Drawing Sheets

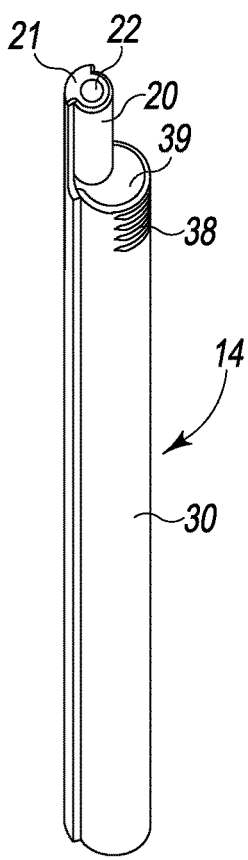
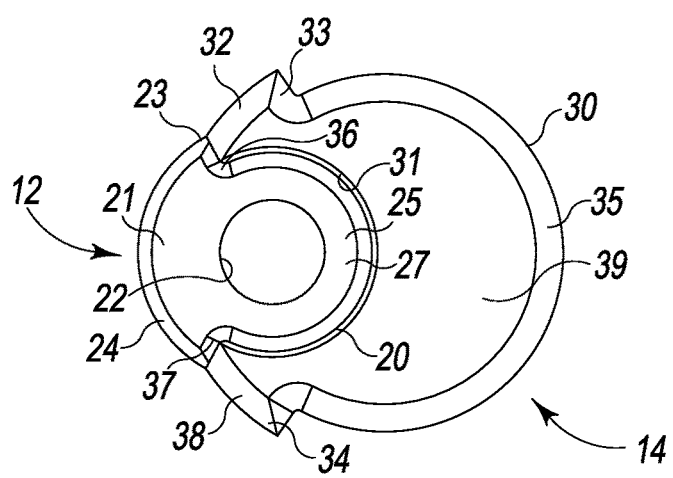
Fig. 4        Fig. 5
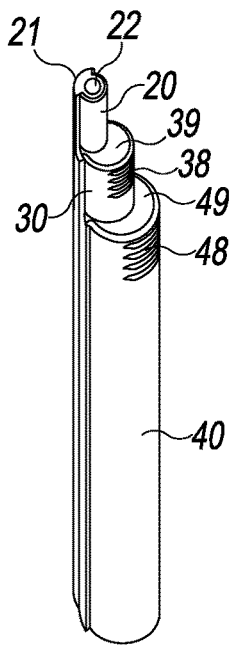
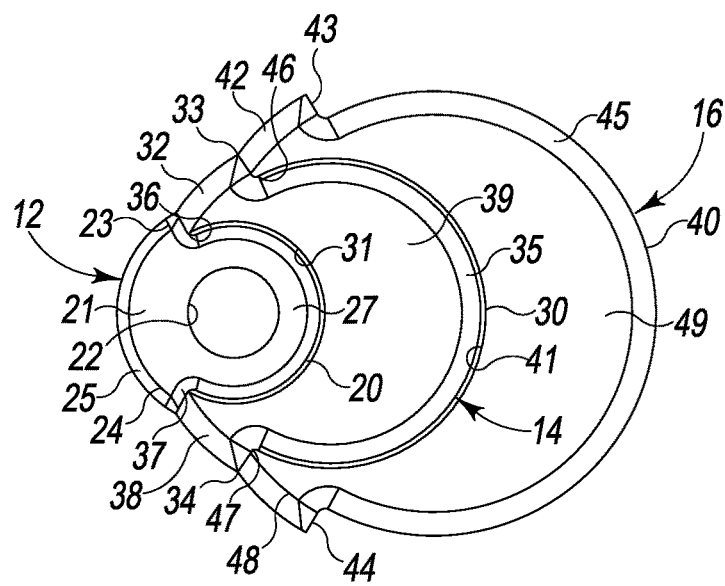
Fig. 6        Fig. 7

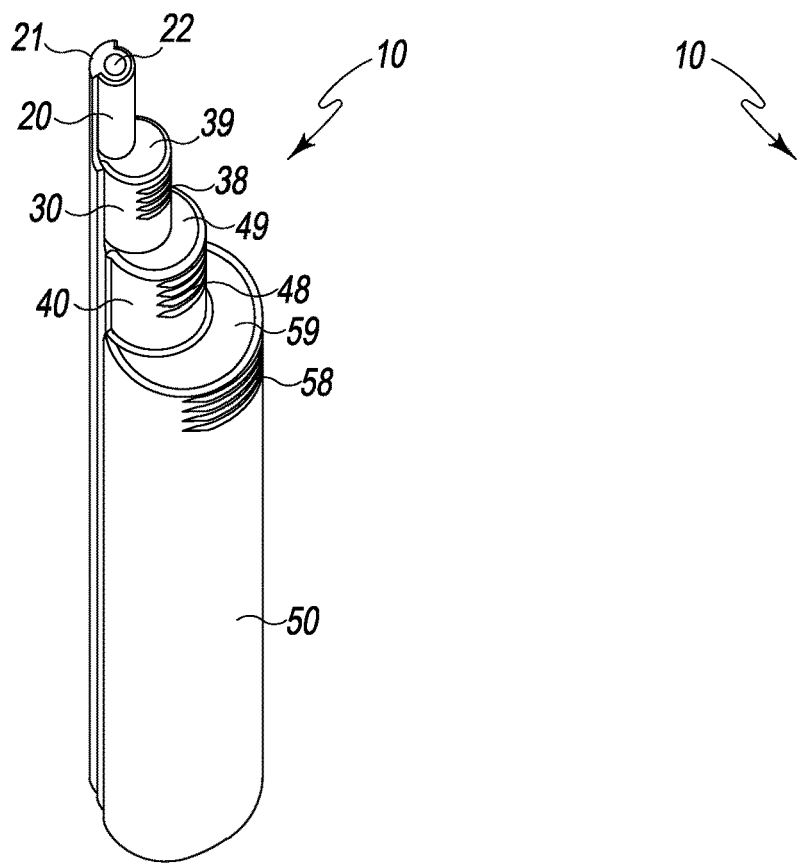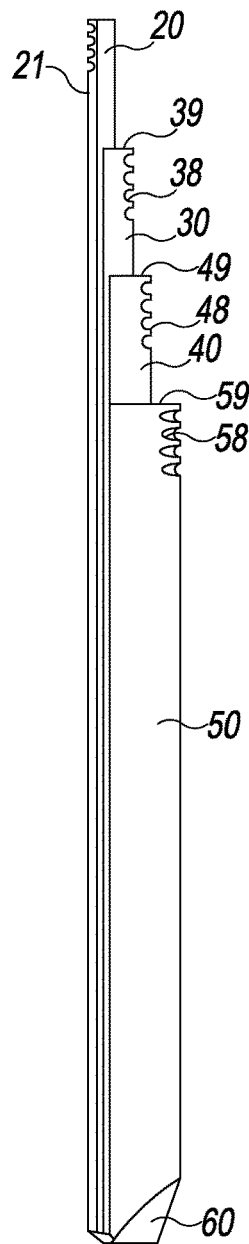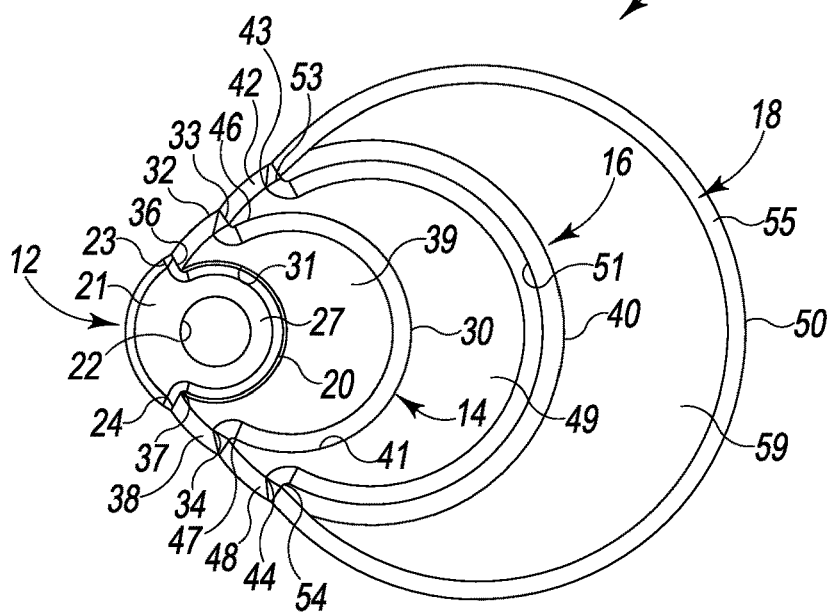
Fig. 8
Fig. 10
Fig. 9

DIRECTIONAL SEQUENTIAL DILATION SYSTEM WITH NEURO MONITORING

CROSS-REFERENCE TO RELATED APPLICATIONS

This application is a continuation-in-part of application Ser. No. 14/135,238, filed Dec. 19, 2013, now U.S. Pat. No. 9,456,846, which claims the benefit of Provisional Application No. 61/739,137, filed Dec. 19, 2012, both of which are incorporated herein by reference in their entireties.

BACKGROUND

The present disclosure relates to devices used in spinal surgery and, more particularly, to devices for neuro monitoring and incision dilation in spinal surgery.

When performing typical spinal surgery it is necessary for the surgeon to contend with and manage various aspects of the procedure. A major aspect of spinal surgery is being able to determine position of a nerve or nerves that are proximate the surgical site. This is necessary to avoid cutting or damaging the nerve or nerves during the surgical procedure.

After an incision is made the surgeon locates any spinal nerve or nerves at or proximate the surgical site (i.e. neuro monitoring) before the soft tissue is dilated in order to gain access to the specific surgical area. Currently, the process of neuro monitoring and then dilating the soft tissue to gain access to the specific surgical site involves using a sequence of right-cylinder dilation tubes of increasing diameters. After an initial or first right-cylinder dilation tube is inserted into the incision for neuro monitoring, additional right-cylinder dilation tubes of increasing diameter are positioned over each other until the specific surgical area is reached.

The problem with the prior art approach is that current sequence of right-cylinder dilation tubes dilate the incision circumferentially which keeps the center point of the initial right-cylinder dilation tube and the main working channel the same. With the prior art method, the surgeon must continually neuro monitor and potentially adjust the position of the working channel since the prior art right-cylinder dilation tubes grow circumferentially in diameter in all directions—which is both towards and away from the nerve position.

It is therefore one object of the present disclosure to overcome the prior art deficiencies of neuro monitoring and incision dilation for spinal surgery.

SUMMARY

A system and method for directional and sequential incision dilation with neuro monitoring uses an assembly of separate nesting tubes. Each dilation tube of the dilation tube assembly is configured to provide incision dilation migration in a given direction, distance and angle from an initial dilation tube of the dilation tube assembly that has been inserted in an initial neuro-monitoring area.

The dilation tube assembly comprises a plurality of cylindrical, nesting dilation tubes including an initial cylindrical dilation tube that provides a passage for a neuro-monitor. Subsequent cylindrical dilation tubes sequentially increase in size along of increasing diameter each one configured to nest onto a previous cylindrical dilation tube via an off-centered channel, notch or cutout formed in each of the subsequent cylindrical dilation tube. The off-centered cutouts allow the subsequent cylindrical dilation tubes to dilate the soft tissue while at the same time migrate the incision dilation in a particular direction at some angle and/or distance from the initial cylindrical dilation tube insertion point (i.e. the initial neuro-monitoring insertion point). Nesting provides a stable construct.

In one form, the initial cylindrical dilation tube is a right-cylinder tube while each subsequent cylindrical dilation tube is an elliptic cylinder tube with a notch or cutout in one wall. The initial dilation tube has a closed passage for a neuro monitoring device. The elliptical configuration provides the directional incision migration. Each notch or cutout is has ends configured and sized to nest onto or fit around a nesting portion of the previous cylindrical dilation tube. Other manners of nesting subsequent cylindrical dilation tubes to provide directional (non-equidistant) incision migration relative to an initial neuro-monitoring insertion point may be used.

The present dilation tube assembly is preferably, but not necessarily, used in conjunction with a spinal retractor during the spinal surgery. The spinal retractor includes a posterior blade that is shaped to receive the dilation tube assembly. The posterior blade may or may not be offered without any angulation capabilities for additional rigidity of the construct. The dilation tube assembly permits determination of nerve position then dilating anteriorly (or away from retractor blades) for a known safe placement of the retractor blades. An arm of the retractor that carries the static blade (and which cradles the dilation tube assembly) includes a threaded table attachment bore along with guide holes posterior of the static blade wall for insertion of a neuro-monitoring sounding probe following insertion of retractor/blades if double checking of nerve is desired.

One embodiment relates to a system for providing access to a surgical site, including a first dilator; a second dilator slidably couplable to a first side of the first dilator and including a first interface portion; a plurality of additional dilators slidably couplable to a second side of the first dilator in a nested manner; and at least one retractor member including a second interface portion removably couplable to the first interface portion; wherein when the first interface portion is coupled to the second interface portion, and the second dilator and the plurality of additional dilators are coupled to the first dilator, the second dilator and the at least one retractor member form a retractor wall extending about the first dilator and the plurality of additional dilators.

Another embodiment relates to a method of providing access to a surgical target, including inserting a first dilator into an incision; coupling a second dilator to a first side of the first dilator; coupling a plurality of additional dilators to a second side of the first dilator opposite the first side; sliding a retractor member into the incision along an exterior surface of at least one of the first dilator, the second dilator, and the plurality of additional dilators; coupling the retractor member to the second dilator; and removing the first dilator and the plurality of additional dilators from the incision.

Another embodiment relates to a system for providing access to a surgical site, including a first dilator; a second directional dilator including a first side slidably couplable to a first side of the first dilator and a second side including a first interface portion; a plurality of additional directional dilators slidably couplable to a second side of the first dilator in a nested manner; and at least one retractor member including a second interface portion removably couplable to the first interface portion; wherein the second directional dilator and the at least one retractor member form a retractor wall extending about the first dilator and the plurality of additional directional dilators.

The present disclosure will be more apparent upon reading the following detailed description in conjunction with the accompanying drawings.

BRIEF DESCRIPTION OF THE DRAWINGS

The above mentioned and other features and objects of the inventive concepts disclosed herein, and the manner of attaining them, will become more apparent and the present disclosure will be better understood by reference to the following description of various embodiments taken in conjunction with the accompanying drawings, wherein:

FIG. 4 is an isometric view of the initial dilation tube and a secondary dilation tube assembled thereon of the exemplary dilation tube system of FIG. 1;

FIG. 5 is an enlarged top view of the assembled initial and secondary dilations tubes of FIG. 4;

FIG. 6 is an isometric view of the initial dilation tube, the secondary dilation tube and a tertiary dilation tube assembled thereon of the exemplary dilation tube system of FIG. 1;

FIG. 7 is an enlarged top view of the assembled initial, secondary and tertiary dilation tubes of FIG. 6;

FIG. 8 is an isometric view of the initial dilation tube, the secondary dilation tube, the tertiary dilation tube and a quaternary dilation tube assembled thereon of the exemplary dilation tube system of FIG. 1;

FIG. 9 is an enlarged top view of the initial, secondary, tertiary and quaternary dilations tubes of FIG. 8;

FIG. 10 is a side view of the assembled initial, secondary, tertiary and quaternary dilations tubes of the present invention;

Like reference numerals indicate the same or similar parts throughout the several figures.

A detailed description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Figure 1:
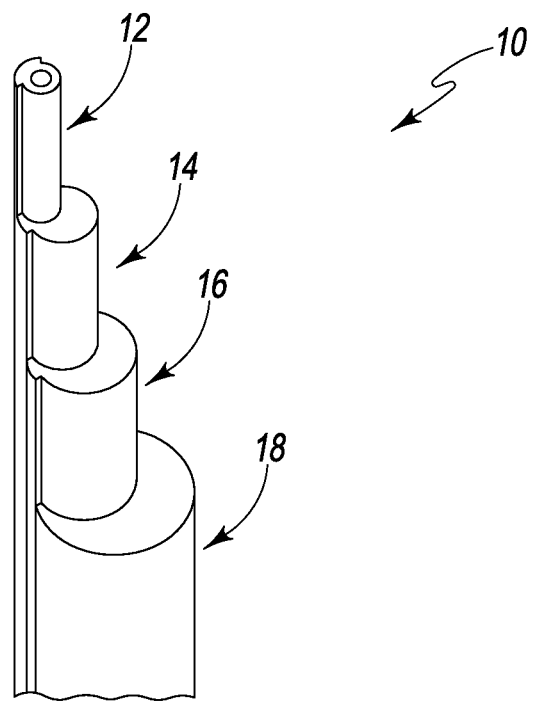
FIG. 1 depicts an exemplary embodiment of an assembled dilation tube system fashioned in accordance with the present principles.

Referring to FIG. 1 there is depicted a view of an upper portion of an exemplary embodiment of a directional sequential dilation tube assembly ("dilation tube assembly"), generally designated 10, fashioned in accordance with the present principles, the dilation tube assembly providing directional and sequential incision dilation migration of a given direction, distance and angle from an initial neuro-monitoring insertion point versus prior art equidistant incision dilation migration from an initial neuro-monitoring insertion point—particularly when used in conjunction with a spinal retractor.

The exemplary embodiment of a dilation tube assembly 10 shown in FIG. 1 and throughout the various figures has four (4) dilation tubes 12, 14, 16 and 18. It should be appreciated that the number of dilation tubes may be more or less than four (4) but can be no less than two (2). The dilation tubes are made from a suitable surgical grade material such as stainless steel, titanium, Aluminum or the like and are preferably, but not necessarily, cylindrical tubes. The cylindrical dilation tube 12 is an initial dilation tube while the cylindrical dilation tubes 14, 16 and 18 are subsequent sequential dilation tubes. Further dilation tubes (not shown) of the dilation tube assembly would be further subsequent sequential dilation tubes. As seen in FIG. 1, the dilation tubes stack upon one another in a nesting fashion such that they are together when assembled. As explained further below, because of their shape the dilation tubes dilate soft tissue of an incision (not shown) while at the same time migrate the incision dilation in a particular direction, distance and angle direction from the initial cylindrical dilation tube insertion point (i.e. the initial neuro-monitoring insertion point as provided by the initial dilation tube) while allowing continuous neuro monitoring via the initial dilation tube from the same location.

Figure 2:
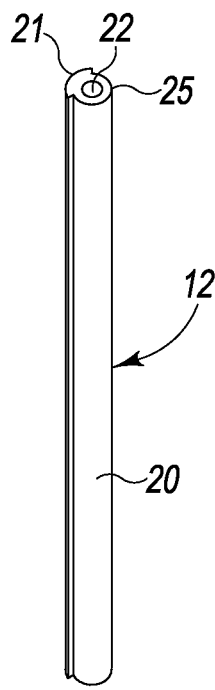
FIG. 2 is an isometric view of an initial dilation tube of the present dilation tube system.
Figure 3:
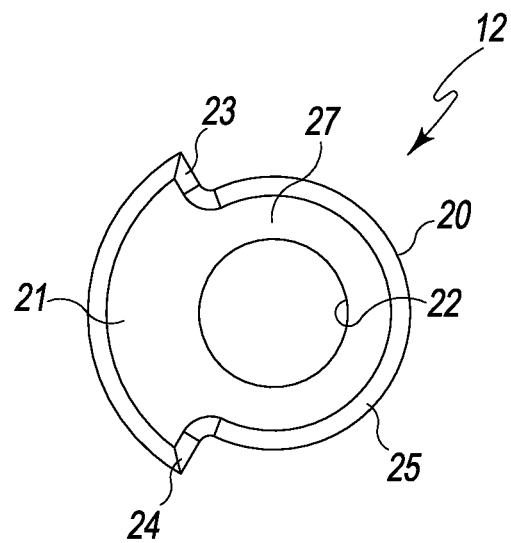
FIG. 3 is an enlarged top view of the initial dilation tube of FIG. 1.

The initial dilation tube 12 is particularly shown in FIGS. 2 and 3. The initial dilation tube 12 is defined by a generally right cylinder body 20 having a rounded longitudinal flange, rib, projection or the like 21 and a longitudinal bore 22. An upper end 27 of the body 20 is generally planar. The longitudinal bore 22 extends the length of the right cylinder body 20 and provides a passage or channel for a neuro probe, device or the like. The initial dilation tube 12 is inserted into the incision such that a neuro monitoring probe, device or the like (or other type of device) 5 extends through the bore 22 (see, e.g., FIG. 16). The outer surface of the body 20 is preferably smooth, including that of the longitudinal rib 21. The outside surface of the body 20, as well as the bodies of the other dilation tubes, may be coated or otherwise made to provide a smooth surface.

Figure 11:
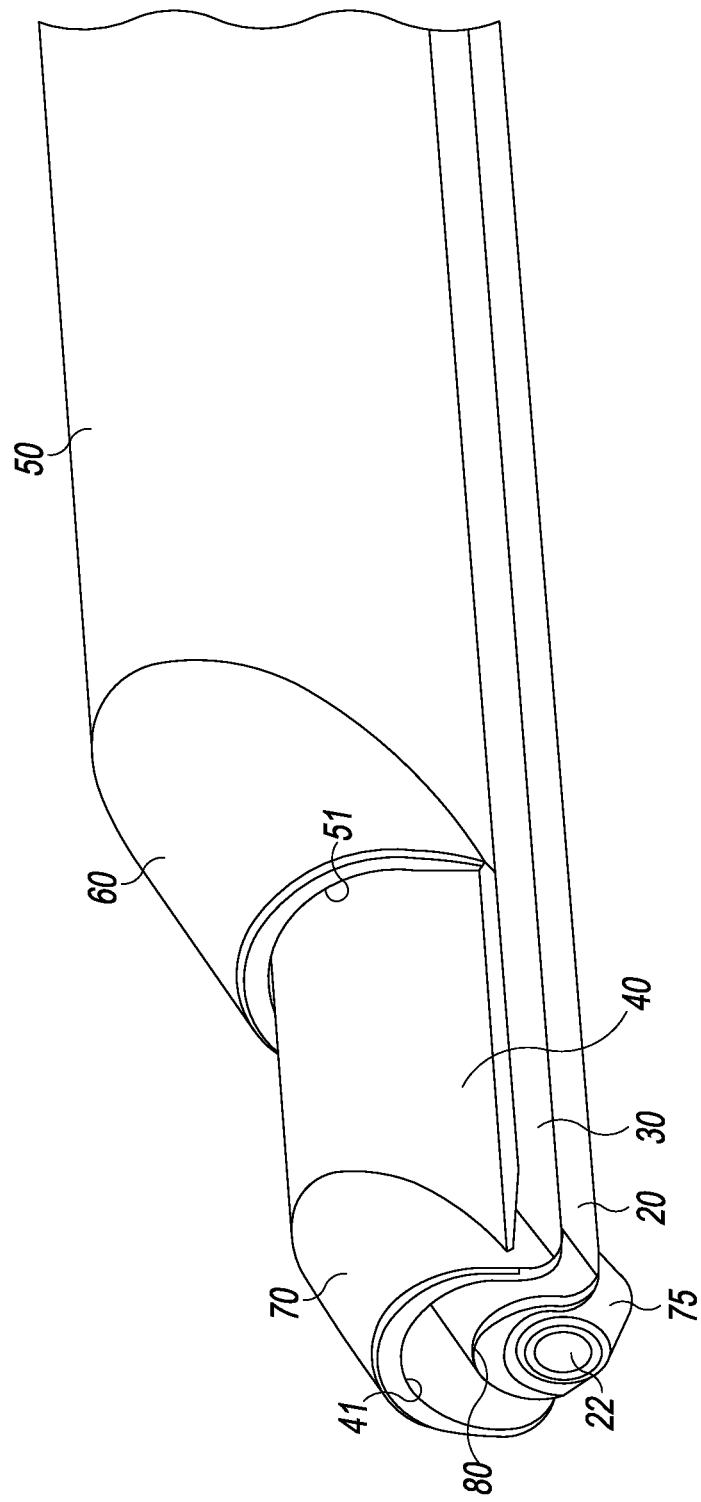
FIG. 11 is an enlarged partial view of the assembled initial, secondary and tertiary dilation tubes with the quaternary dilation tube having a beveled tip shown being slid over the tertiary dilation tube.

In FIG. 3, an enlarged view of a top of the initial dilation tube 12 is shown to particularly envision its longitudinal and cross-sectional shape and/or configuration. As discerned, the longitudinal flange 21 has a rounded outer surface in like manner and preferably, but not necessarily, concentric with the outer surface of the body 20. A beveled or angled edge 25 provides a transition between the upper ends of the body 20 and the longitudinal rib 21. The longitudinal rib 21 extends from the body 20 at a first longitudinal transition 23 on one side of the rib 21 and at a second longitudinal transition 24 on another side of the rib 21. The first longitudinal transition 23 creates or defines a first shelf or ledge providing a first seat for a first subsequent dilation tube 14. The second longitudinal transition 24 creates or defines a second shelf or ledge providing a second seat for the first subsequent dilation tube 14. As seen in FIG. 11, the initial dilation tube 12 has a rounded lower end 75.

The dilation tube 12 is the first or initial tube of the dilation tube assembly to be inserted into the incision. The bore 22 of the initial dilation tube 12 permits a monitoring probe 5 or the like to be positioned adjacent a nerve or nerves (neuro-monitoring) once an incision has been made and/or positional stability through which a guide wire, probe, device or the like can be inserted. In this first stage of incision dilation, the initial dilation tube 12 inserted into the incision is preferably, but not necessarily, generally a right-cylinder so as to initially provide a generally equidistant incision dilation area.

Referring to FIGS. 4 and 5 there is depicted a second stage in assembly of the dilation tube structure 10 wherein the first subsequent directional dilation tube 14 is sequentially situated onto the initial dilation tube 12. The outer shape and configuration of the initial dilation tube 12 allows the nested reception of the first subsequent directional dilation tube 14 via its nesting structures. The first subsequent directional dilation tube 14 is defined by a generally elliptic cylinder body 30 having a generally elliptical outer surface and a rounded longitudinal notch, cutout, channel or the like 31. An upper end 39 of the body 30 is generally planar. The longitudinal channel 31 extends the length of the elliptic cylinder body 30 and provides a reception site for the initial dilation tube 12 as the first subsequent directional dilation tube 14 is received onto the initial dilation tube 12 during the second stage of incision dilation per the present method. The outer surface of the body 30 is preferably smooth, including the inner surface of the longitudinal channel 31. An upper portion of the outer surface of the body 30 may include arced notches 38.

Referring to FIG. 5, an enlarged view of a top of the first subsequent directional dilation tube 14 is shown to particularly envision its longitudinal and cross-sectional shape and/or configuration. As discerned, the longitudinal channel 31 has a rounded inner surface, shape and size complementary to the outer surface of the body 20 of the initial dilation tube 12 in order to be received on or nest upon the initial dilation tube 12. The nesting structures include a first longitudinal flange 32 provided at a first edge or end 36 of the channel 31 and a second longitudinal flange 38 provided at a second edge or end 37 of the channel 31. The shape of the first end 36 is complementary to the shape of the first transition 23 such that the first end 36 of the first subsequent dilation tube 14 seats or nests against the first transition 23 of the initial dilation tube 12. The shape of the second end 37 is complementary to the shape of the second transition 24 such that the second end 37 of the first subsequent directional dilation tube 14 seats or nests against the second transition 24 of the initial dilation tube 12. A beveled or angled edge 35 provides a transition between the upper ends of the body 30 and first and second flanges 32, 38.

The first flange 32 extends from the body 30 at a first longitudinal transition 33 and is generally arc-shaped and preferably, but not necessarily, concentric with the outer surface of the body 30. The second flange 38 extends from the body 30 at a second longitudinal transition 34 and is generally arc-shaped and preferably, but not necessarily, concentric with the outer surface of the body 30. The first longitudinal transition 33 creates or defines a first shelf or ledge providing a first seat for a second subsequent directional dilation tube 16. The second longitudinal transition 34 creates or defines a second shelf or ledge providing a second seat for the second subsequent dilation tube 16. As seen in FIG. 11, the first subsequent directional dilation tube 14 has a rounded lower end 80.

The first subsequent directional dilation tube 14 is configured as an elliptical cylinder with the channel 31 disposed in a side thereof. As such the tube 14 has an elliptic portion 39 that projects outwardly from the channel 31. Direction of the elliptic portion 39 provides the direction of incision dilation. Rotational orientation of the initial dilation tube 12 determines the angle and direction of incision dilation by the orientation of the first and second transitions 23, 24 since the first subsequent directional dilation tube nests onto the initial dilation tube 12.

The first subsequent directional dilation tube 14 is the second dilation tube to be inserted into the incision. The bore 22 of the initial dilation tube 12 still permits monitoring position of the nerve or nerves (neuro-monitoring) while the incision is dilated away from the nerve (e.g. anteriorly) in the desired angle as determined by the rotational orientation of the initial dilation tube 12. In this second stage of incision dilation, the first subsequent directional dilation tube 14 inserted over the initial dilation tube 12 and into the incision. The elliptical configuration of the body 30 migrates the incision dilation towards the direction of the ellipse.

Referring to FIGS. 6 and 7 there is depicted a third stage in assembly of the dilation tube structure 10 wherein the second subsequent directional dilation tube 16 is situated onto the first subsequent directional dilation tube 14. The outer shape and configuration of the first subsequent directional dilation tube 14 allows nested reception of the second subsequent directional dilation tube 16. The second subsequent directional dilation tube 16 is defined by a generally elliptic cylinder body 40 having a rounded outer surface and a rounded longitudinal notch, cutout, channel or the like 41. An upper end 49 of the body 40 is generally planar. The longitudinal channel 41 extends the length of the elliptic cylinder body 40 and provides a reception site for the first subsequent directional dilation tube 14 as the second subsequent directional dilation tube 16 is received onto the first subsequent directional dilation tube 14 during the third stage of incision dilation per the present method. The outer surface of the body 40 is preferably smooth, including the inner surface of the longitudinal channel 41. An upper portion of the outer surface of the body 30 may include arced notches 48.

Referring to FIG. 7, an enlarged view of a top of the second subsequent directional dilation tube 16 is shown to particularly envision its longitudinal and cross-sectional shape and/or configuration. As discerned, the longitudinal channel 41 has a rounded inner surface, shape and size complementary to the outer surface of the body 30 of the first subsequent directional dilation tube 14 in order to be received on the first subsequent directional dilation tube 14. Nesting structures include a first longitudinal flange 42 provided at a first edge or end 46 of the channel 41 and a second longitudinal flange 48 provided at a second edge or end 47 of the channel 41. Others are provided, including the shape of the first end 46 being complementary to the shape of the first transition 33 such that the first end 46 of the second subsequent directional dilation tube 16 seats or nests against the first transition 33 of the first subsequent dilation tube 14. The shape of the second end 47 is complementary to the shape of the second transition 34 such that the second end 47 of the second subsequent directional dilation tube 16 seats or nests against the second transition 34 of the first subsequent directional dilation tube 14. A beveled or angled edge 45 provides a transition between the upper ends of the body 40 and first and second flanges 42, 48.

The first flange 42 extends from the body 40 at a first longitudinal transition 43 and is generally arc-shaped and preferably, but not necessarily, concentric with the outer surface of the body 40. The second flange 48 extends from the body 40 at a second longitudinal transition 44 and is generally arc-shaped and preferably, but not necessarily, concentric with the outer surface of the body 40. The first longitudinal transition 43 creates or defines a first shelf or ledge providing a first seat for a third subsequent dilation tube 18. The second longitudinal transition 44 creates or defines a second shelf or ledge providing a second seat for the third subsequent directional dilation tube 18. As seen in FIG. 11, the second subsequent directional dilation tube 16 has a beveled lower end 70.

The second subsequent directional dilation tube 16 is configured as an elliptical cylinder with the channel 41 disposed in a side thereof. As such the tube 16 has an elliptic portion 49 that projects outwardly from the channel 41. Direction of the elliptic portion 49 provides the direction of incision dilation which coincides with the direction of the elliptic portion 39 of the first subsequent directional dilation tube 14.

The second subsequent directional dilation tube 16 is the third dilation tube to be inserted into the incision. The bore 22 of the initial dilation tube 12 still permits monitoring position of the nerve or nerves (neuro-monitoring) while the incision is further dilated away from the nerve (e.g. anteriorly) in the desired angle as determined by the rotational orientation of the initial dilation tube 12. In this third stage of incision dilation, the second subsequent directional dilation tube 16 inserted over the first subsequent directional dilation tube 14 and into the incision. The elliptical configuration of the body 40 further migrates the incision dilation towards the direction of the ellipse. The nesting structures provide a stable construct. Moreover, the nesting structures allow one dilation tube to be precisely assembled onto the previous dilation tube from the vertical position, essentially vertically sliding one dilation tube onto the other dilation tube.

Referring to FIGS. 8 and 9 there is depicted a fourth, and with this embodiment of dilation tube assembly, a final stage in assembly of the dilation tube structure 10 wherein the third subsequent directional dilation tube 18 is situated onto the second subsequent directional dilation tube 16. The outer shape and configuration of the second subsequent directional dilation tube 16 allows nested reception of the third subsequent directional dilation tube 18 in like manner to the previous dilation tubes. The third subsequent directional dilation tube 18 is defined by a generally elliptic cylinder body 50 having a rounded outer surface and a rounded longitudinal notch, cutout, channel or the like 51. An upper end 59 of the body 50 is generally planar. The longitudinal channel 51 extends the length of the elliptic cylinder body 50 and provides a reception site for the second subsequent directional dilation tube 16 as the third subsequent directional dilation tube 18 is received onto the second subsequent directional dilation tube 16 during the fourth stage of incision dilation per the present method. The outer surface of the body 50 is preferably smooth, including the inner surface of the longitudinal channel 51. An upper portion of the outer surface of the body 50 may include arced notches 58.

Referring to FIG. 9, an enlarged view of a top of the third subsequent dilation tube 18 is shown to particularly envision its longitudinal and cross-sectional shape and/or configuration. As discerned, the longitudinal channel 51 has a rounded inner surface, shape and size complementary to the outer surface of the body 40 of the second subsequent dilation tube 16 in order to be received on the second subsequent dilation tube 16. A first edge 53 is provided at a first end of the channel 51, while a second edge 54 is provided at a second end of the channel 51. Again, the tube has nesting structures. The shape of the first end 53 is complementary to the shape of the first transition 43 such that the first end 53 of the third subsequent directional dilation tube 18 seats or nests against the first transition 43 of the second subsequent directional dilation tube 16. The shape of the second end 54 is complementary to the shape of the second transition 44 such that the second end 54 of the third subsequent directional dilation tube 18 seats or nests against the second transition 4 of the second subsequent directional dilation tube 16. A beveled or angled edge 55 provides a transition between the upper ends of the body 50 and first and second ends 53, 54. As seen in FIG. 11, the third subsequent directional dilation tube 18 has a beveled lower end 60.

The third subsequent directional dilation tube 18 is configured as an elliptical cylinder with the channel 51 disposed in a side thereof. As such the tube 18 has an elliptic portion 59 that projects outwardly from the channel 51. Direction of the elliptic portion 59 provides the direction of incision dilation which coincides with the direction of the elliptic portion 49 of the second subsequent directional dilation tube 16.

The third subsequent directional dilation tube 18 is the fourth (and here, final) dilation tube to be inserted into the incision. The bore 22 of the initial dilation tube 12 still permits monitoring position of the nerve or nerves (neuro-monitoring) while the incision is further dilated away from the nerve (e.g. anteriorly) in the desired angle as determined by the rotational orientation of the initial dilation tube 12. In this fourth stage of incision dilation, the third subsequent directional dilation tube 18 inserted over the second subsequent directional dilation tube 16 and into the incision. The elliptical configuration of the body 50 further migrates the incision dilation towards the direction of the ellipse. FIG. 10 depicts a side view of all of the dilation tubes assembled (i.e. the present dilation tube assembly 10).

It should be appreciated that more subsequent dilation tubes having like configurations may be position between the initial dilation tube and the final dilation tube.

Figure 12:
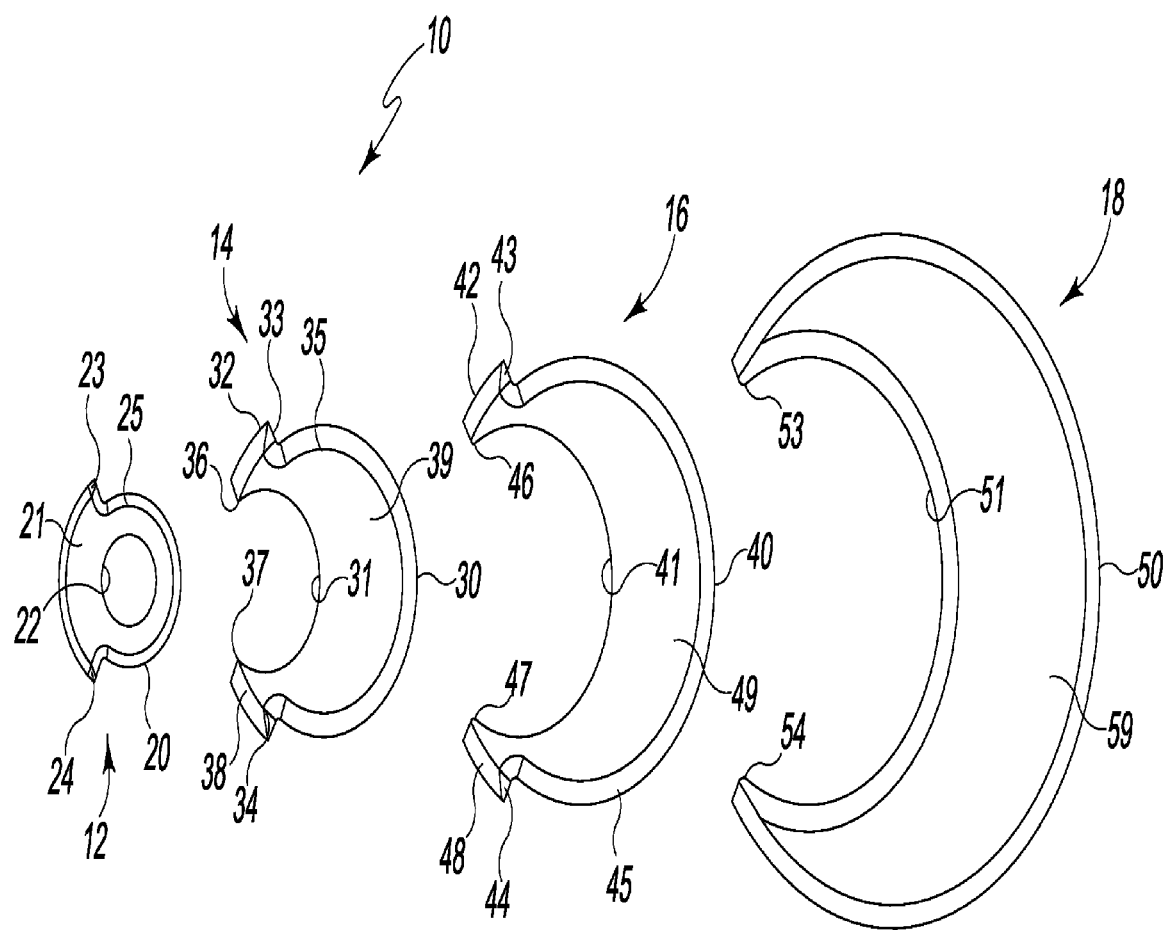
FIG. 12 is a top exploded view of the initial, secondary, tertiary and quaternary dilations tubes.

FIG. 12 shows the four directional dilation tubes in an exploded view to illustrate how the various dilation tubes are received on one another and nest together.

Figure 13:
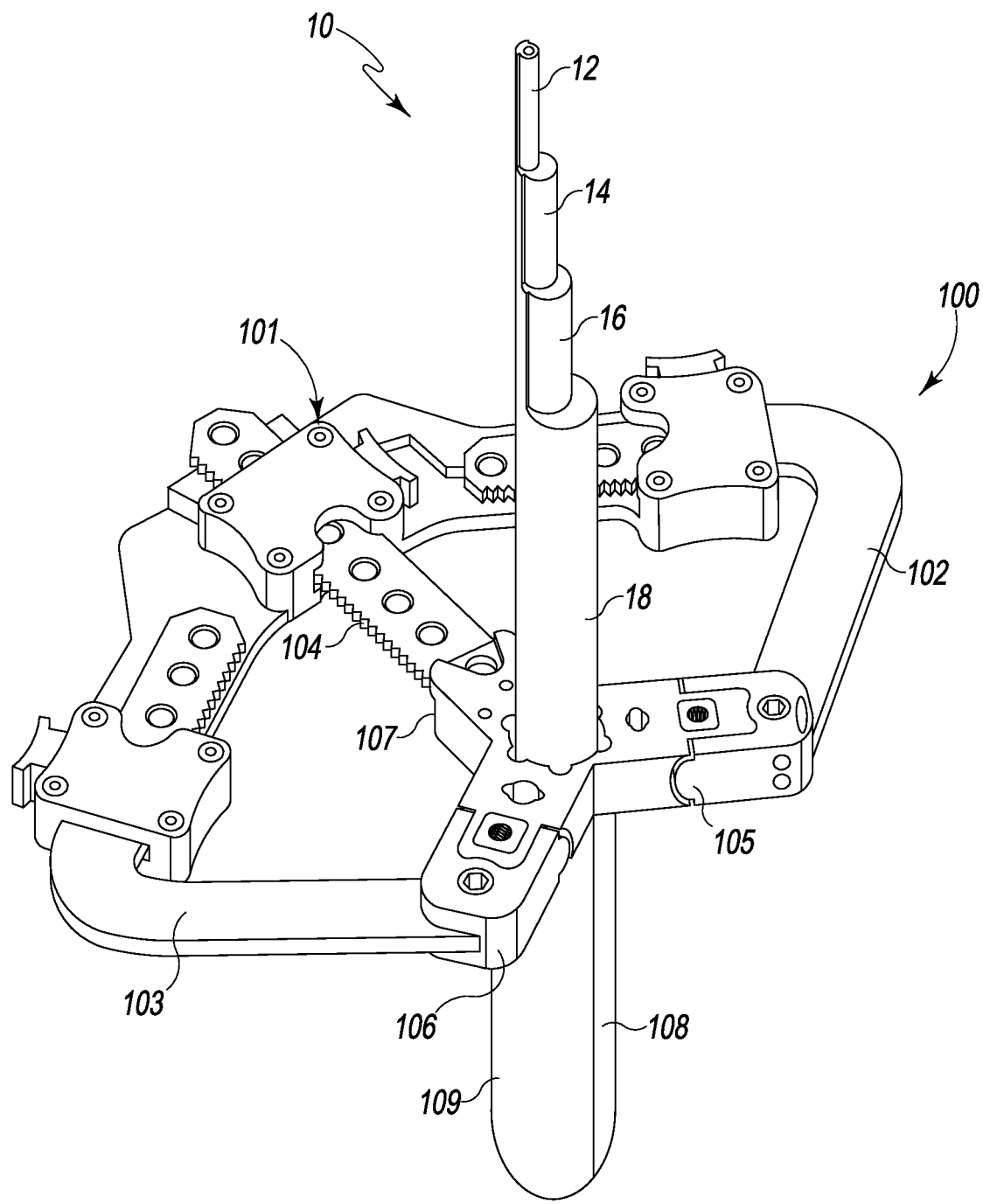
FIG. 13 is an isometric view of a spinal retractor holding the dilation tube system of FIG. 1.
Figure 14:
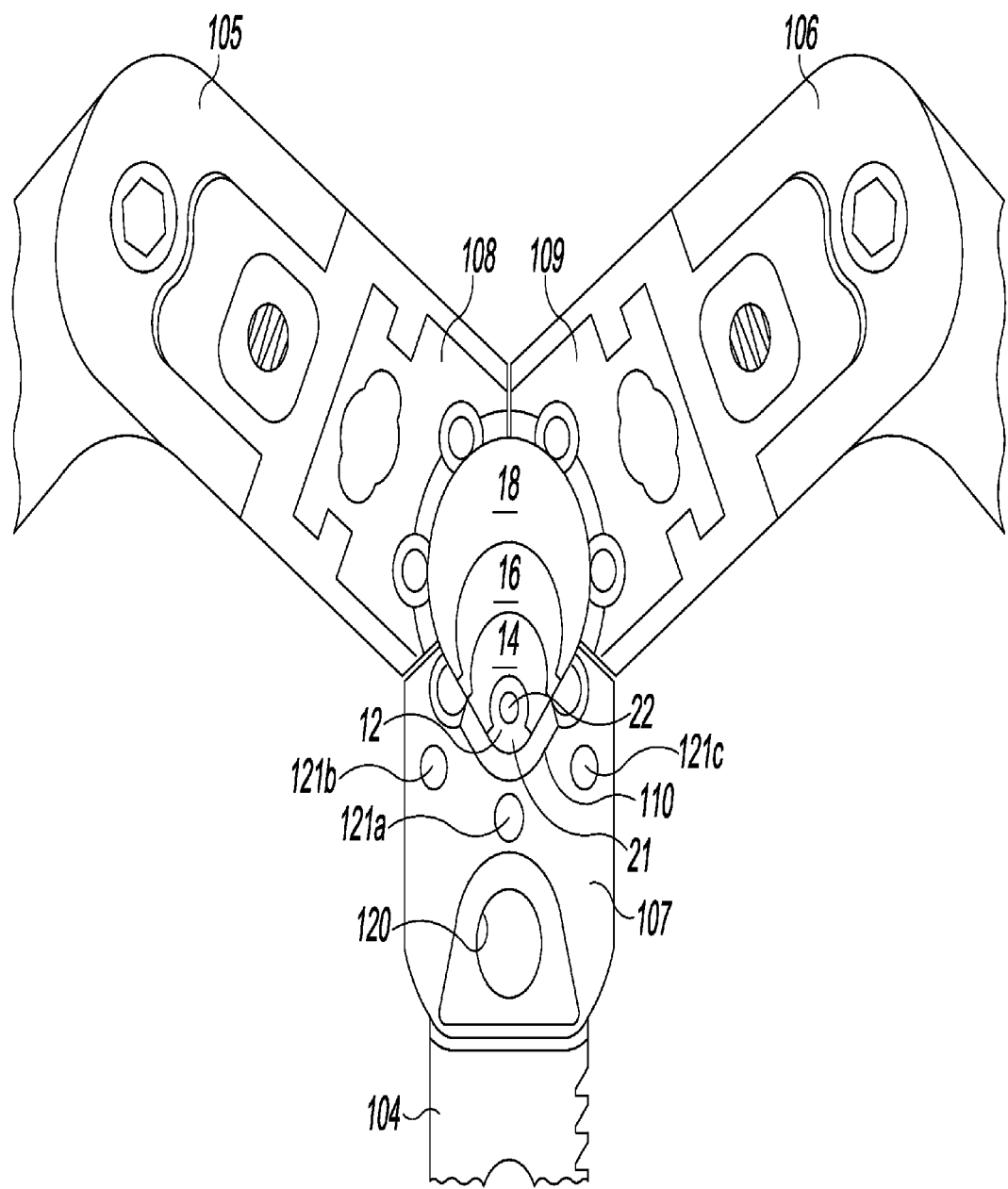
FIG. 14 is an enlarged top view of a portion of the spinal retractor holding the dilation tube system of FIG. 13.

FIGS. 13 and 14 show the spinal retractor 100 holding the present directional dilation tube assembly 10. The retractor 100 has a body 101 that is configured to be mounted relative to a spine patient via a threaded bore (or attachment location) 120 of the static arm 107 of the body 101. The body 101 has a first adjustable arm 102 that holds an articulating portion 105, and a second adjustable arm 103 that holds an articulating portion 106. The articulating portion 105 is configured to receive a blade 108, while the articulating portion 107 is configured to receive a blade 109. The arm 104 may or may not be static regarding articulation and holds the configured blade 110. The arm 104 may also have guide holes 121*a*, 121*b*, and 121*c* posterior of the wall of the static blade 110 for insertion of a neuro-monitoring sounding probe following insertion of the retractor blades if double checking of nerve position is desired. The arm 104 may hold the blade 110 static such that the blade 110 has no angulation capabilities for additional rigidity of the construct.

A more complete description of a spinal retractor such as can be used in place of retractor 100, with the exception of a static posterior blade 110, is found in U.S. patent application Ser. No. 13/720,800 filed Dec. 19, 2012, the specification of which is specifically incorporated herein by reference.

Figure 15:
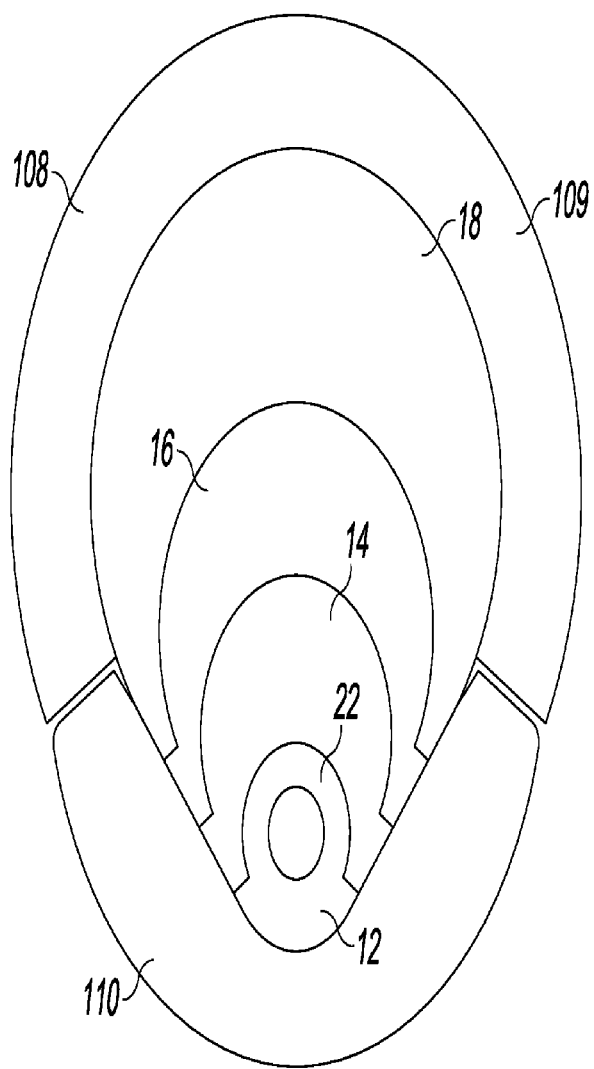
FIG. 15 is an enlarged cross sectioned top view of the present assembled dilation tube system surrounded by blades of the spinal retractor particularly illustrating the directional dilation migration at a given distance or angle from an initial insertion point achieved by the present dilation tube system.

FIG. 15 is an illustration depicting the directional dilation tube assembly 10 surrounded by the blades 108, 109 and 110 of the retractor 100 particularly showing the configuration of the static blade 110 for receiving the stacked configuration of dilation tubes 12, 14, 16, 18. As easily discerned, the bore 22 of the initial dilation tube 12 permits monitoring position of a nerve or nerves while migrating the incision dilation towards the elliptic portions of the tubes.

Figure 16:
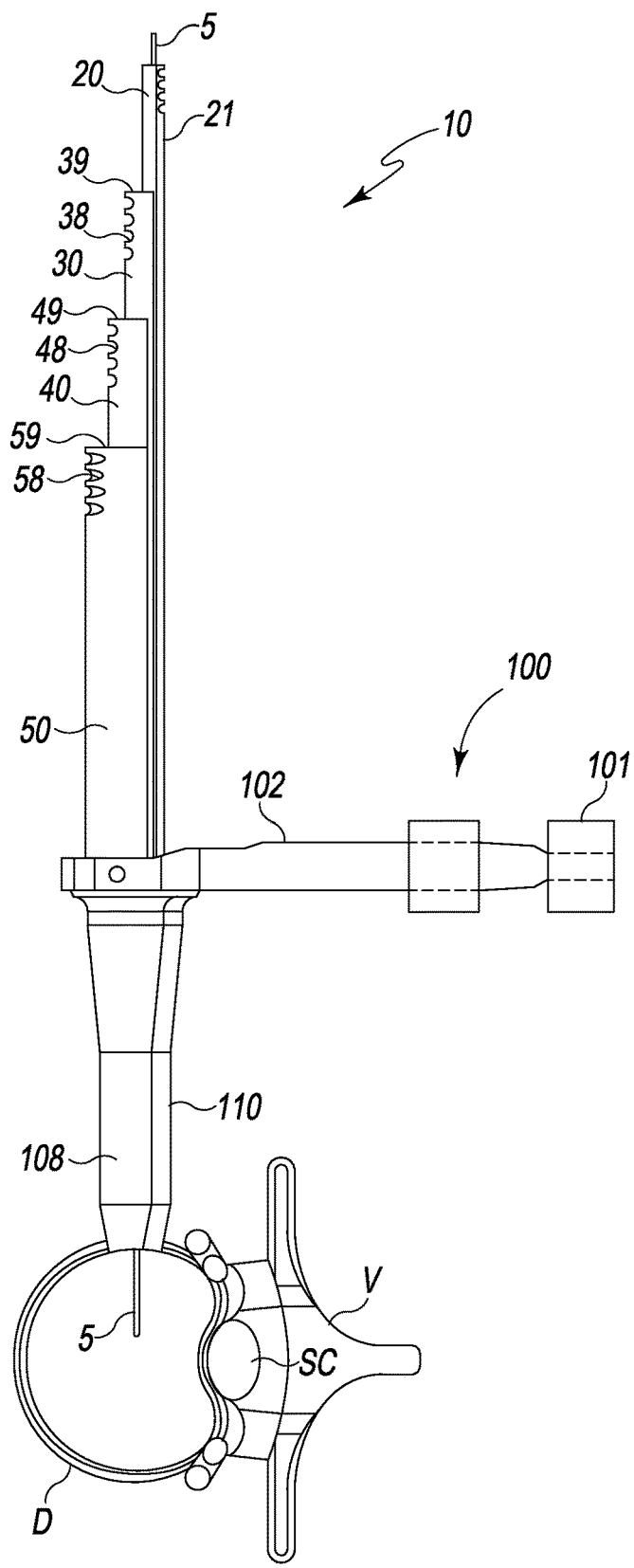
FIG. 16 is a side view of the present assembled dilation tube system with an inserted neuro probe held by the spinal retractor of FIG. 15 relative to a vertebral section of a patient.

FIG. 16 shows the directional dilation tube assembly 10 held by the retractor 100 relative to a human vertebral section, particularly a vertebra V, spinal column SC, and vertebral disc D. The directional dilation tube assembly 10 has been fully assembled and a neuro monitoring probe, device or the like 5 extends through the bore 22 of the initial dilation tube 12 from an upper end of the body 20 to a lower end of the body 20. FIG. 16 provides an exemplary manner of using the present directional dilation tube assembly 10.

Referring now to FIGS. 17-42, an alternative embodiment of a directional system for providing dilation and/or distraction includes a dilator assembly and a retractor assembly.

Figure 17:
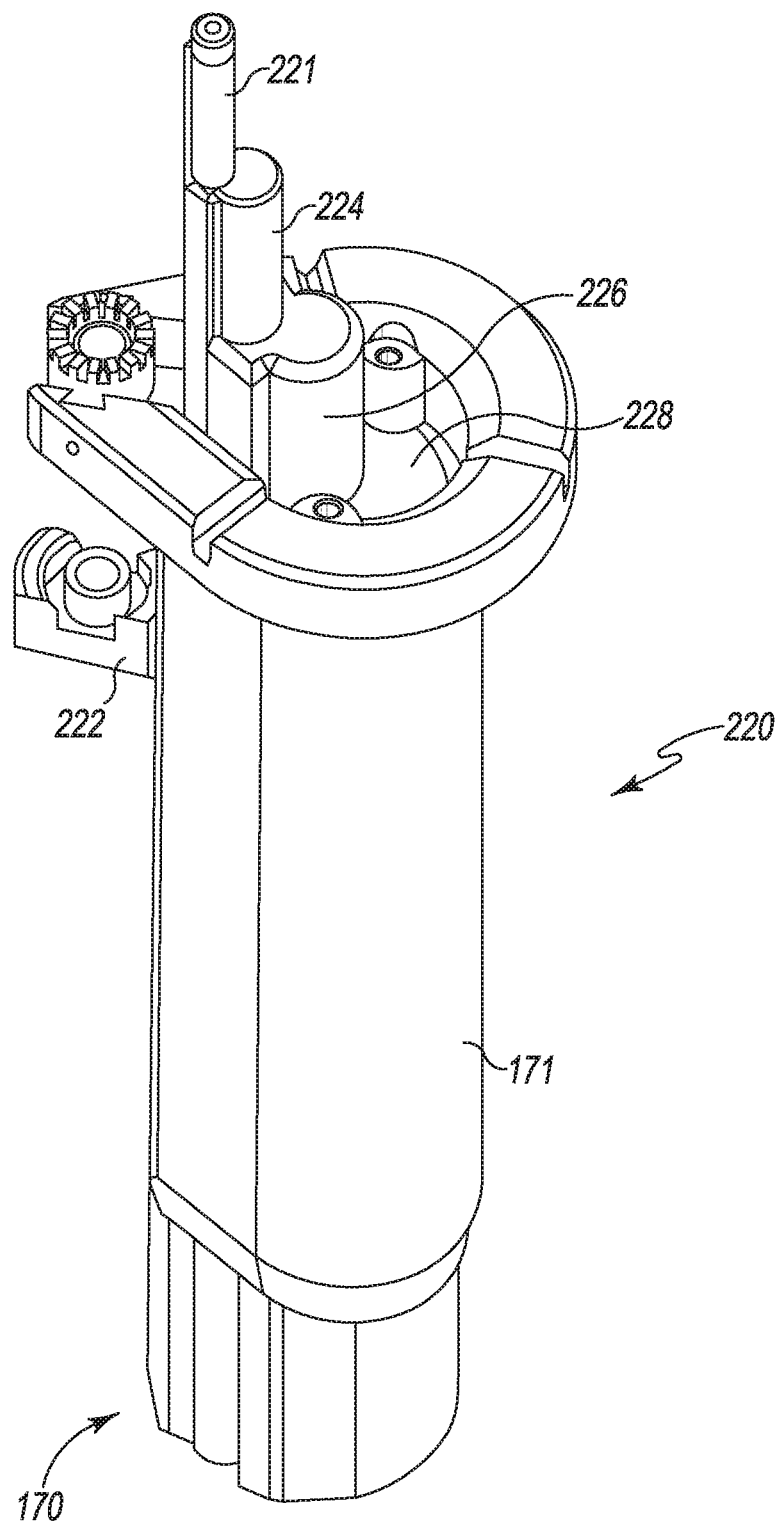
FIG. 17 is an isometric view of an alternative embodiment of a system including an assembled dilation system and retractor assembly.

Referring to FIG. 17, a direction sequential dilator assembly 220 and a retractor assembly 170 are shown. Dilator assembly 220 and retractor assembly 170 collectively provide a system for providing access to a surgical site. Dilator assembly 220 provides directional and sequential incision dilation migration of a given direction, distance, and angle from an initial neuro-monitoring insertion point versus prior art equidistant incision dilation migration from an initial neuro-monitoring insertion point—particularly when used in conjunction with retractor assembly 170. As discussed in detail below, dilator assembly 220 includes a plurality of dilation members, or dilators (e.g., elongated members, nesting members), shown as a first dilator 221, a second dilator 222 and a plurality of additional dilators 224, 226, 228.

Figure 18:
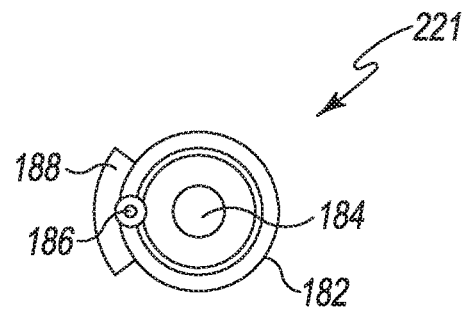
FIG. 18 is a top view of a dilator of the system of FIG. 17 according to one embodiment.

Referring to FIG. 18, a top view of first dilator 221 is shown. First dilator 221 is defined by right cylinder body 182. Cylindrical bore 184 is concentric with right cylinder body 182 and creates a passage through the length of first dilator 221. Neuro-monitoring element 186 is located to one side of cylindrical bore 184. Neuro-monitoring element 186 may include a conductive element or other sensor device running the length of first dilator 221. A neuro-monitoring sensor or other device may also be passed through cylindrical bore 184. Dovetail connector 188 extends from one side of cylinder body 182 and runs all or a portion of the length of first dilator 221.

Figure 19:
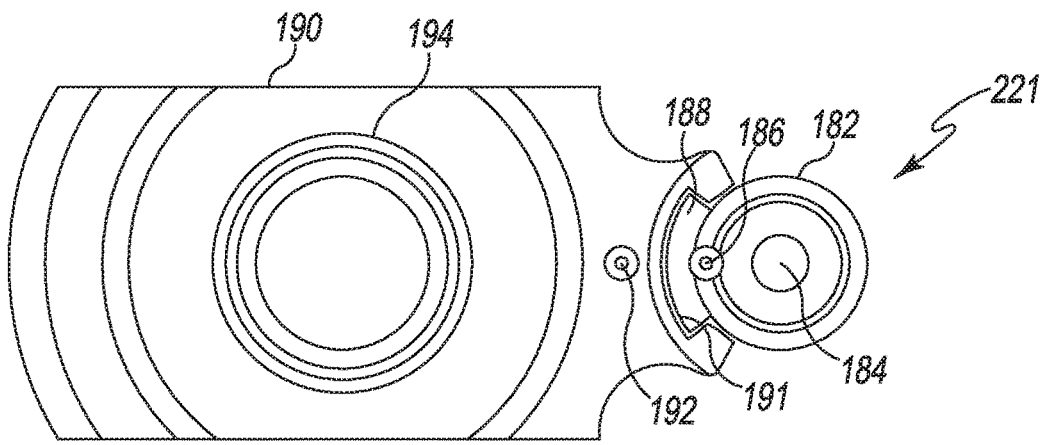
FIG. 19 is a top view of a portion of the system of FIG. 17 according to one embodiment.

Referring to FIG. 19, a top view of the first dilator 221 coupled to second dilator 222 is shown according to one embodiment. Dovetail connector 188 of first dilator 221 fits into dovetail receiver 191 or second dilator 222, slidably securing the first dilator 221 to the second dilator 222. Neuro-monitoring element 192 is located adjacent to and to one side of dovetail receiver 191, and may include a conductive element or other sensor device running the length of second dilator 222. As shown in FIG. 19, dovetail connector 188 and dovetail receiver 191 are complimentary in shape to prevent lateral and/or movement between the components, and while FIG. 19 shows a dovetail-like interface, other interfaces that limit the relative movement of the components (e.g., to sliding relative movement) may be used according to various alternative embodiments.

Second dilator 222 also includes docking feature or docking element 190 (e.g., a first interface). Docking feature 190 includes docking cylinder 194, top portion 196, and lower portion 198. Docking cylinder 194 may be internally threaded to receive a table mount feature (see FIGS. 40-42). Docking cylinder 194 may be concentric within a ring defined by beveled edge 197 separating top portion 196 and lower portion 198. In one embodiment, docking element 190 is generally aligned with dovetail receiver 191.

Figure 20:
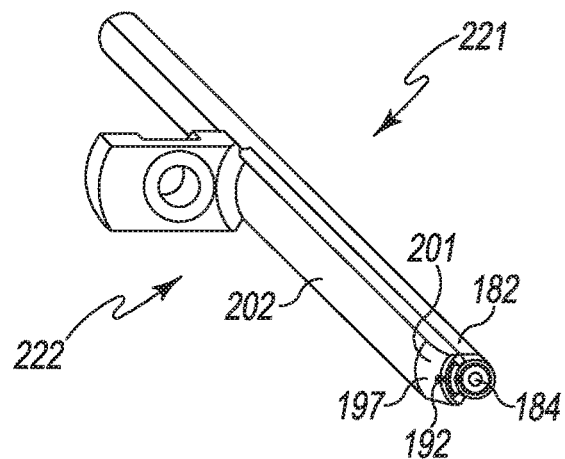
FIG. 20 is an isometric view of a portion of the system of FIG. 17 according to one embodiment.
Figure 21:
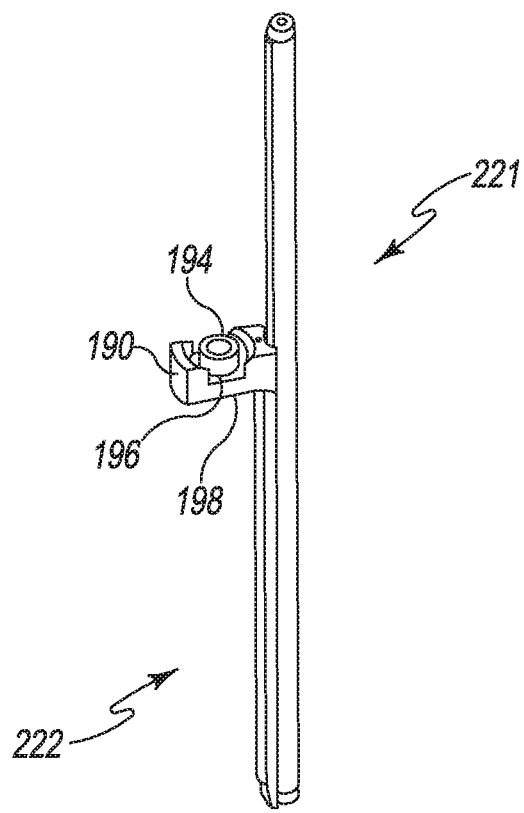
FIG. 21 is another isometric view of a portion of the system of FIG. 17 according to one embodiment.

Referring now to FIGS. 19-21, first dilator 221 includes cylinder body 182, cylindrical bore 184, and neuro-monitoring element 186. Neuro-monitoring element 192 is provided on second dilator 222. Second dilator 222 is further shown to have dilator shaft 202 and beveled bottom end 201. Docking element 190 extends at a right angle from the top of dilator shaft 202. First dilator 221 is capable of sliding relative to second dilator 222 along dovetail receiver 191.

Figure 22:
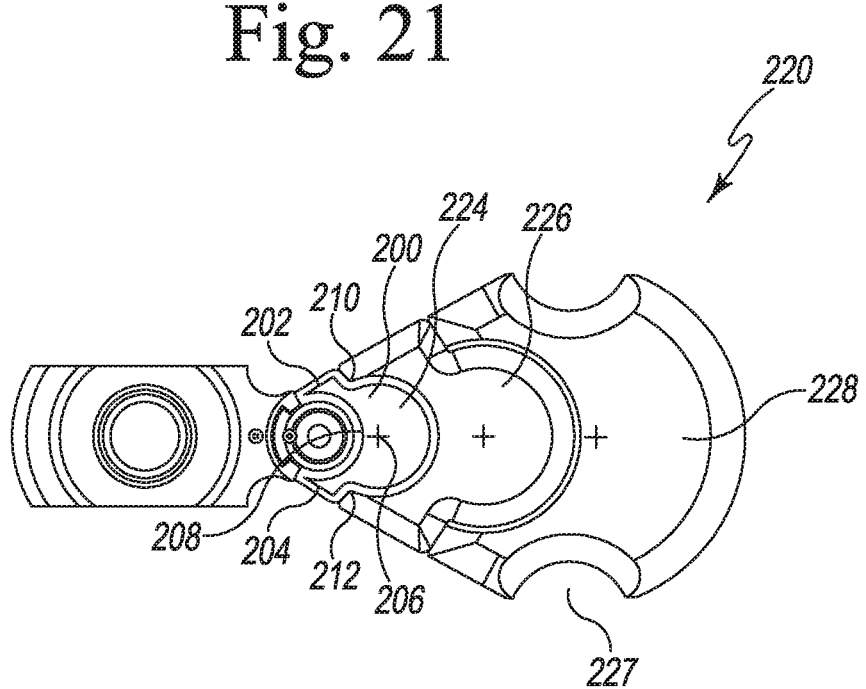
FIG. 22 is a top view of a plurality of dilators of the system of FIG. 17 according to one embodiment.

Referring now to FIG. 22, a top view of dilator assembly 220 is shown. As shown, the dilator assembly 220 includes first dilator 221, second dilator 222, and additional dilators 224, 226, 228. Other embodiments may involve a different number of dilators.

In one embodiment, dilator 224 includes a circular portion 200 defining a center point 206. Side portions 202, 204 extend from either side of circular portion 200 and define side recesses 210, 212. A receiver portion 208 is at least partially circular in shape to receive a circular portion of an adjacent dilator (e.g., dilator 221). Dilator 224 is elongated and includes a beveled end 214.

Dilator 226 is substantially similar in shape to dilator 224, but is enlarged relative to dilator 224 such that the amount of dilation provided increases between dilator 224 and dilator 226. Dilator 228 is likewise similar in shape and enlarged in size relative to dilator 226. In addition, the side recesses 227 of dilator 228 are a different shape from side recesses 210, 212, and are sized to accommodate corresponding features on retractor assembly 170. As shown in FIG. 22, the side portions of the additional dilators 224, 226, 228 generally form a continuous sidewall that generally conforms to the inner surface of retractor assembly 170.

Center point 206 of circular portion 200 is shifted away from the central axis of the first dilator 221, defining a directional offset that provides the direction of dilation. Rotational orientation of the first dilator 221 determines the angle and direction of incision dilation by determining the direction of the offset of dilator 224. As seen in FIG. 22, the center points of the circular portions of additional dilators 224, 226, 228 are generally in line with the center of first and second dilators 221, 222, such that second dilator 22 and additional dilators 224, 226, 228 extend from first dilator 221 in generally opposite directions in one embodiment. As shown throughout the figures, the various dilators generally slidably engage adjacent other dilators in a nesting fashion, and include beveled lower edges to facilitate insertion into an incision.

Figure 23:
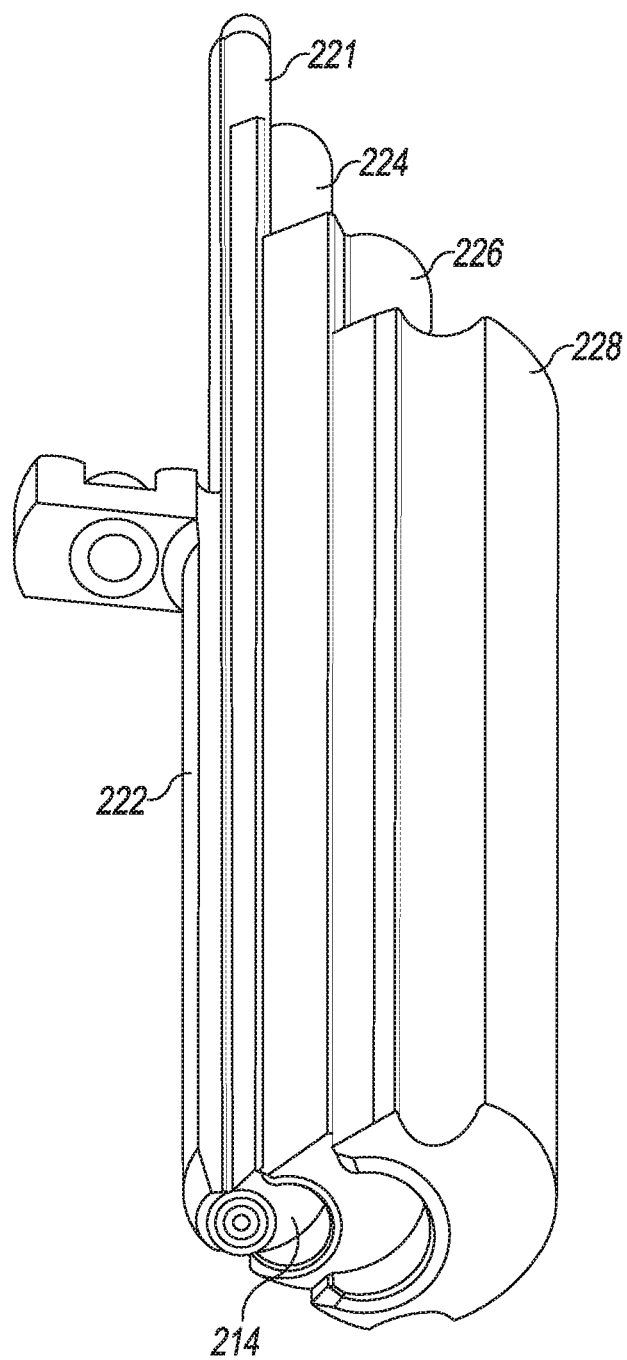
FIGS. 23-26 are isometric views of the plurality of dilators of FIG. 22 according to various embodiments.
Figure 24:
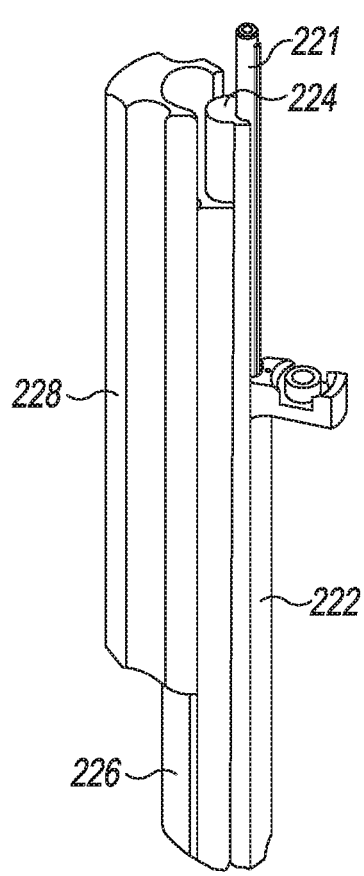
Figure 25:
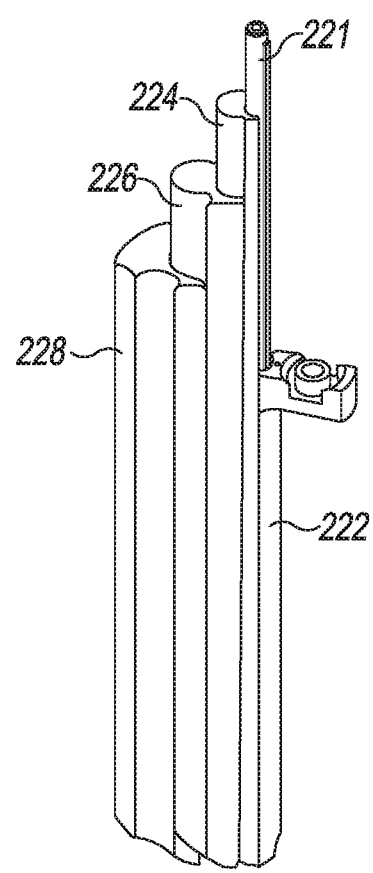
Figure 26:
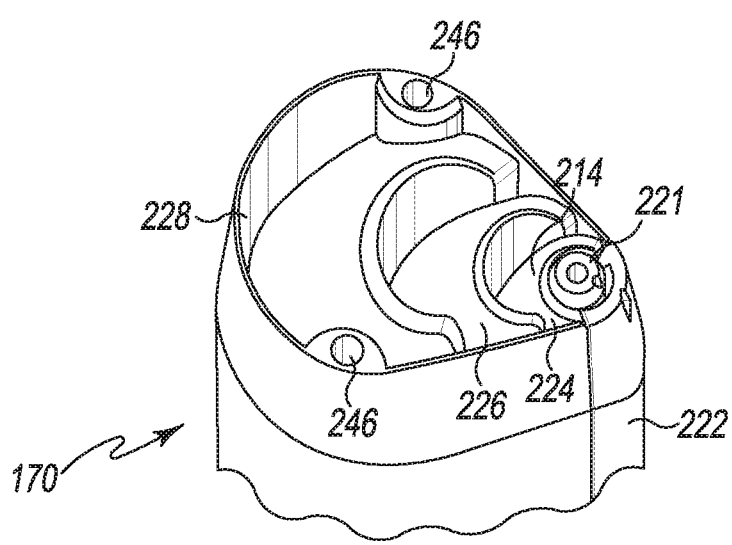
Figure 27:
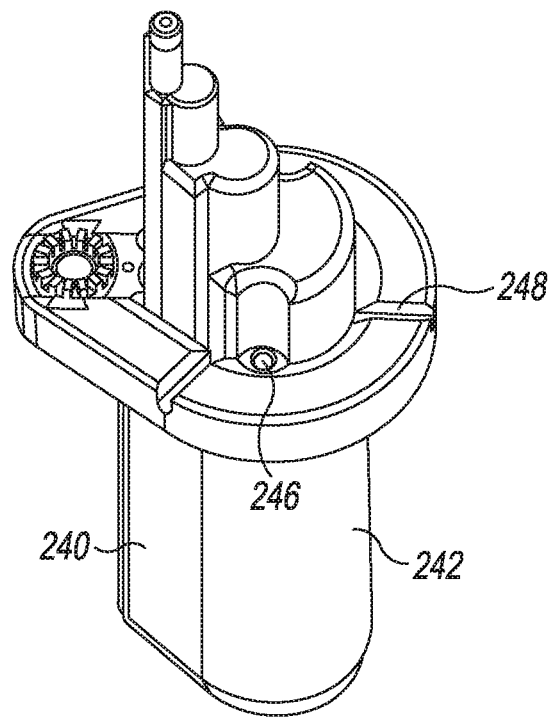
FIGS. 27-29 are isometric views of the system of FIG. 17 according to various embodiments.

As shown in FIG. 23, dilators 224, 226, and 228 extend downward end in beveled bottom ends such as beveled bottom 214. Dilator assembly 220 can be used to dilate an incision by first inserting first dilator 221 and second dilator 222, using the neuro-monitoring elements 186, 192 of each to determine a direction for dilation, rotating first dilator 221 so that dilator 224 is offset in the desired direction, and inserting the remaining dilators 226, 228 sequentially. Neuro-monitoring element 186 of first dilator 221 and neuro-monitoring element 192 of second dilator 222 may be used cooperatively, alternatively, or otherwise to determine the location of a nerve relative to the incision and the dilation system. FIG. 23 shows one embodiment of dilator assembly 220 as fully deployed at the end of dilation. FIGS. 24-25 show additional views of dilator assembly 220.

Referring to FIGS. 26-33, in one embodiment, after fully deploying dilator assembly 220, retractor assembly 170 is configured to slidably engage dilator assembly 220. Retractor assembly 170 includes retractor member 171 (e.g., a retractor wall or wall portion), top portion 172, and docking element 173. Beveled bottom edge 244 helps retractor member 171 slide into an incision. Retractor member 171 includes flat portions 240 and curved portion 242. In some embodiments, flat portions 240 and curved portion 242 generally match all or a portion of the inner surface of dilator assembly 220. Curved portion 242 substantially matches the curved portion of dilator 228, while flat portions 240 correspond to the side portions of dilators 224, 226, 228. Curved portion 242 and flat portions 240 combine to form a horseshoe shape with an open end opposite curved portion 242. Second dilator 222 and retractor member 171 collectively form a retractor wall (e.g., a closed loop) extending about dilators 221, 224, 226, 228.

Figure 28:
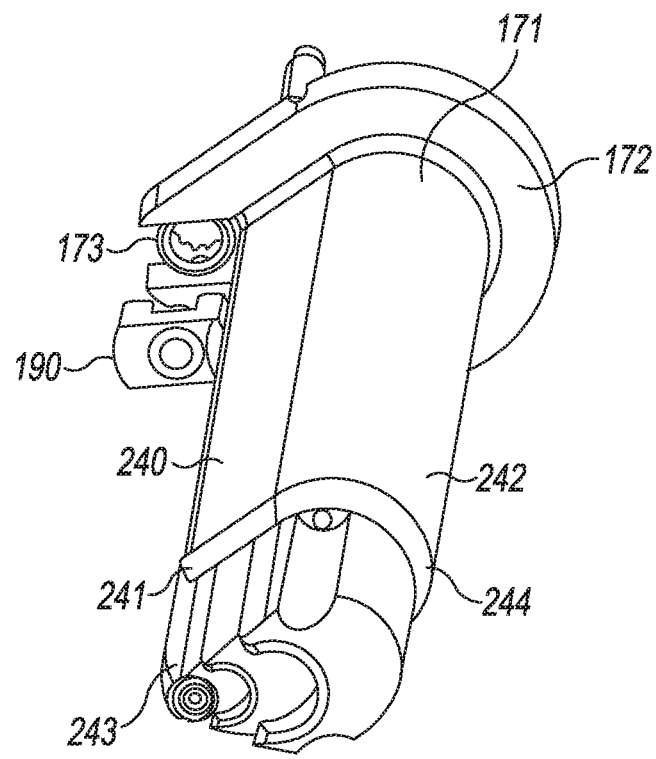
Figure 29:
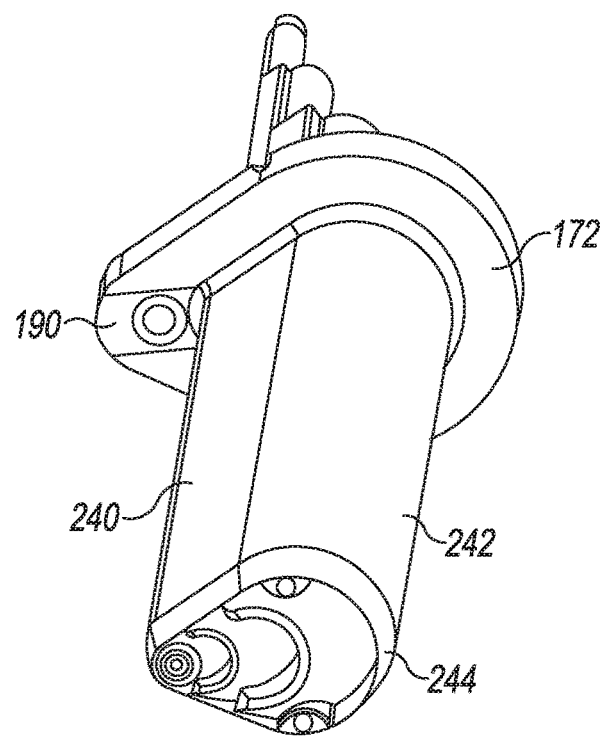
Figure 40:
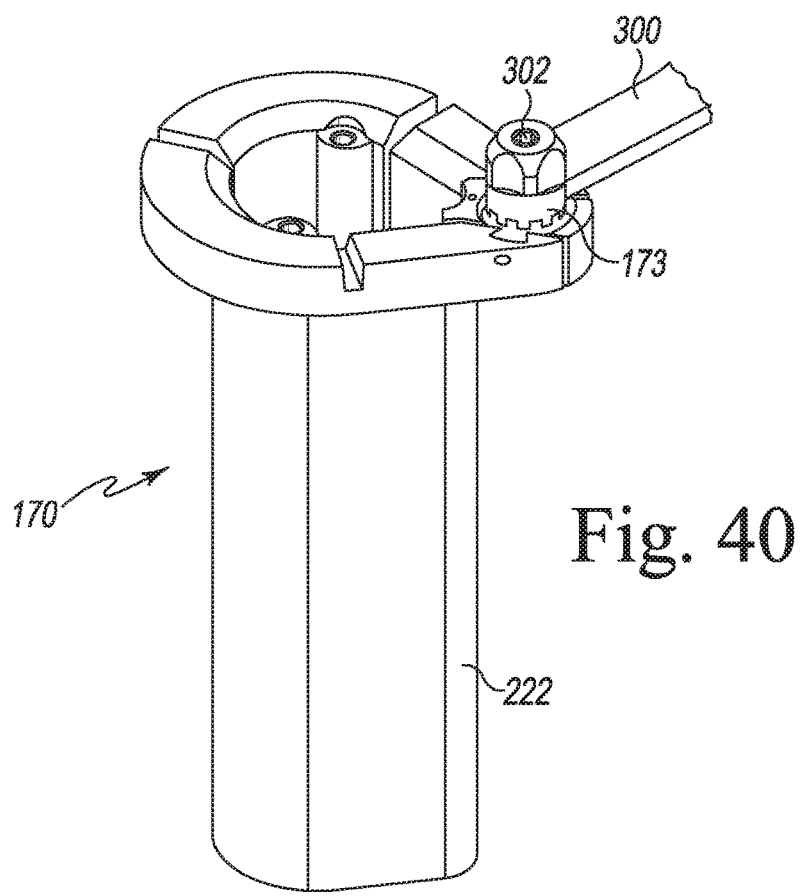
FIGS. 40-42 are views of the retractor of the system of FIG. 17 coupled to a table mount according to one embodiment.
Figures 41, 42:
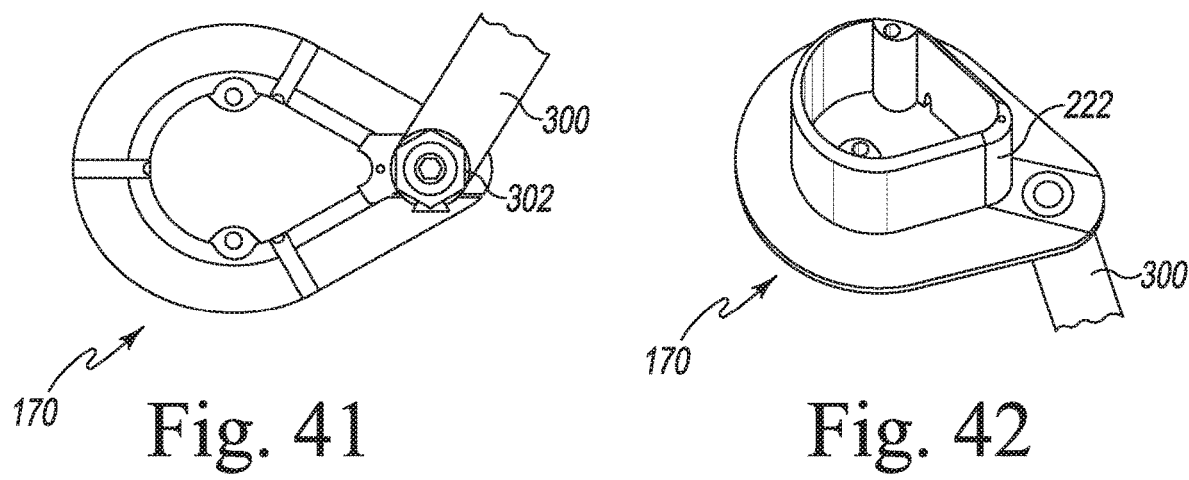

As shown in FIG. 28, docking element 173 is aligned above docking element 190 as retractor assembly 170 slides onto dilator assembly 220. Docking element 173 includes a ring-shaped structure such that docking element 173 fits securely into the space (e.g., an annular space) between docking cylinder 194 and the surrounding portion of docking feature 190. Docking element 173 and docking feature 190 couple retractor assembly 170 to second dilator 22. When second dilator 222 is docked to retractor assembly 170, flat portions 240 of retractor member 171 are joined at one end by curved portion 242 and at the other end by dilator shaft 202 of second dilator 222. In one embodiment, retractor member 171 includes end portions or lobes 241 provided on opposing sides that are received in recesses or channels 243 on second dilator 222. In some embodiments, lobes 241 and channels 243 extend along all or a portion of the lengths of retractor member 171 and second dilator 222. In further embodiments, lobes 241 and channels 243 have complimentary shapes and are configured to prevent splaying of retractor member 171 during use. Docking element 173 and docking feature 190 can be secured to a table, bed, or stand by a mounting feature (see, e.g., FIGS. 40-42) that connects to docking cylinder 194 in order to substantially immobilize retractor assembly 170 and second dilator 222. For example, FIGS. 40-42 show a table arm 300 secured to docking element 173 and docking feature 190 using a locking element 302 (e.g., a locking nut).

Figure 30:
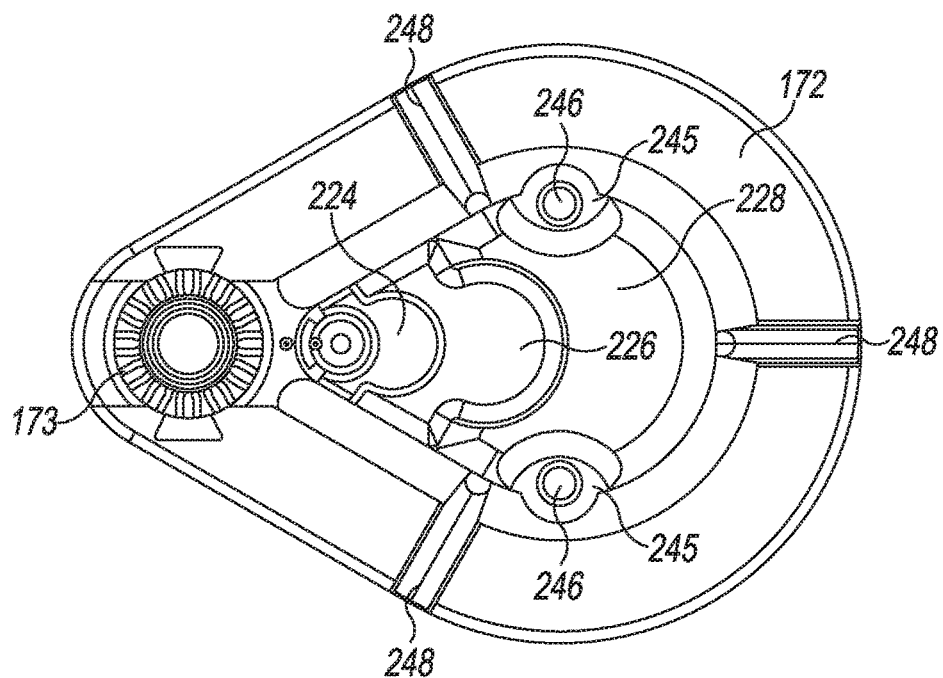
FIG. 30 is a top view of the system of FIG. 17 according to one embodiment.
Figure 31:
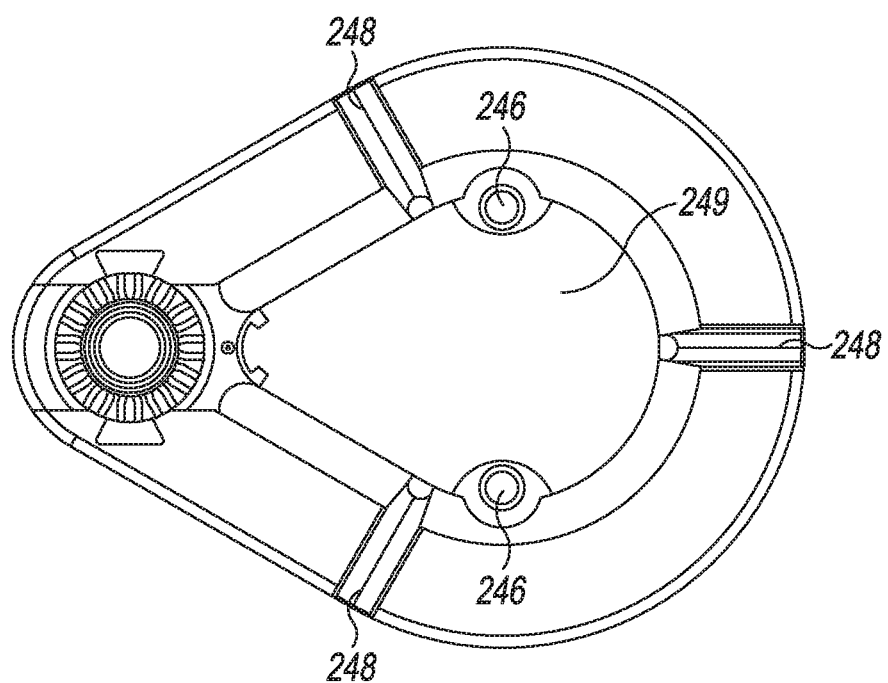
FIG. 31 is a top view of a portion of the system of FIG. 17 according to one embodiment.
Figure 32:
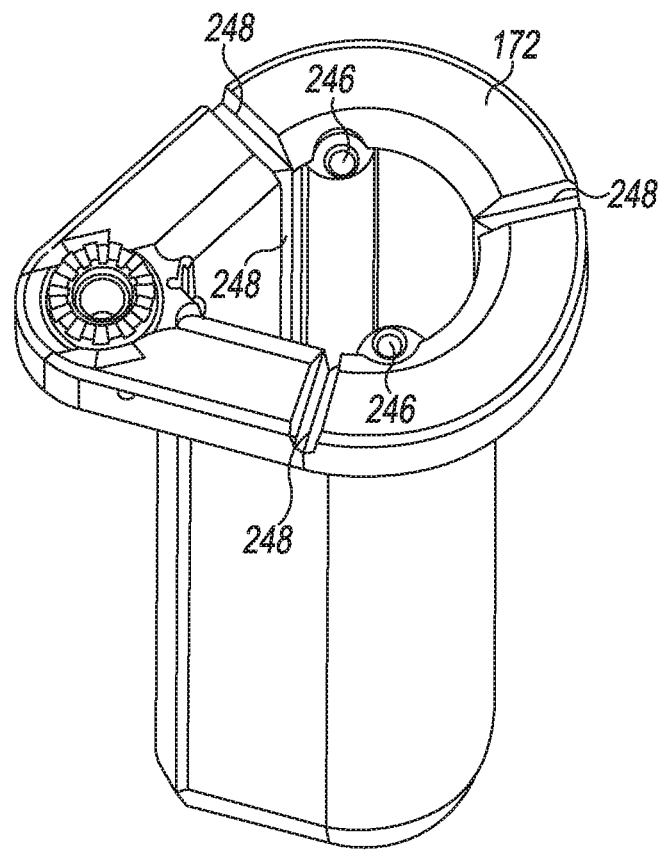
FIG. 32 is an isometric view of a portion of the system of FIG. 17 according to one embodiment.
Figure 33:
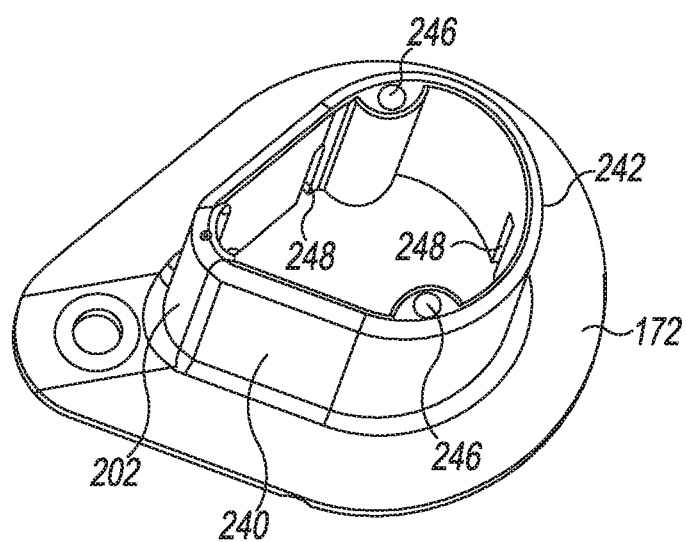
FIG. 33 is an isometric distal view of a portion of the system of FIG. 17 according to one embodiment.

Referring to FIGS. 30-32, top portion 172 of retractor member 171 extends around additional dilators 224, 226, 228 such that an inner surface of retractor member 171 substantially conforms to the peripheral surface formed by the nesting of dilators 224, 226, 228. The inner surface of retractor member 171 includes protruding portions 245 that include fixation apertures 246. In one embodiment, fixation apertures 246 are elongated channels extending all or a portion of the length of retractor member 171 to enable placement of fixation wires, pins, rods, etc. Protruding portions 245 are received within the side recesses of dilator 228. Top portion 172 further includes one or more channels 248 configured to hold and/or retain lighting members. For example, as shown in FIG. 30, top portion 172 include 3 generally equally spaced channels 248. Each channel 248 may further extend down all or a portion of the inner surface of retractor member 171, as shown in FIG. 32.

Removal of dilators 221, 224, 226, 228 creates working channel 249 through which a surgeon can access an area of surgical interest. Second dilator 222 remains with retractor member 171, forming a retractor wall extending about the area of interest. Working channel 249 is defined by the combination of the retractor member 171 and dilator shaft 202 of second dilator 222, with dilator shaft 202 closing the open end of the horseshoe shape created by flat portions 240 and curved portion 242. Working channel 249 may be provided with a light source along light channels 248 in top portion 172 and running down retractor member 171.

Figure 34:
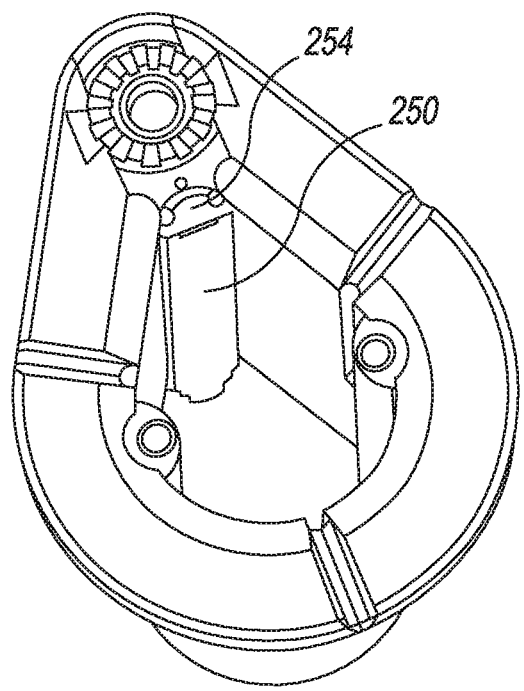
FIG. 34 is an isometric view of the system of FIG. 17 and an intradiscal shim according to one embodiment.
Figure 35:
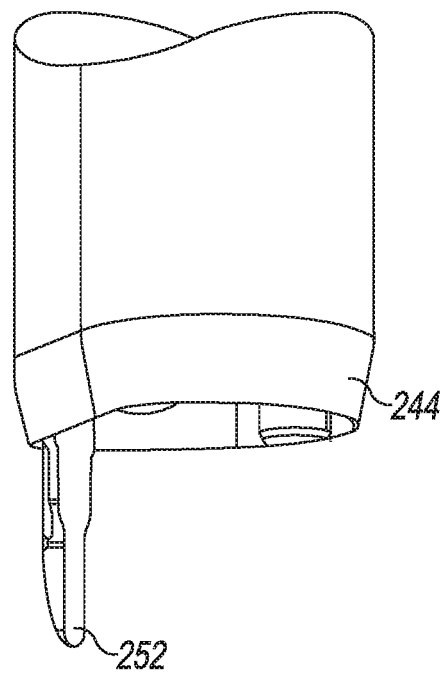
FIG. 35 is an isometric view of the intradiscal shim of FIG. 34 according to one embodiment.

Referring now to FIGS. 34-35, an intradiscal shim 250 may be used to further secure retractor assembly 170 to the patient and provide stability to avoid movement of working channel 249 during surgery. Intradiscal shim 250 may be connected to second dilator 222 using a dovetail projection 254 received in dovetail receiver 191, or may connect directly to retractor assembly 170. Intradiscal shim 310 includes rounded bottom tip 252 for insertion into a patient's disc space. Shim 310 is slidable relative to second dilator 222 to enable insertion, adjustment, securement, and removal of shim 310.

Figure 36:
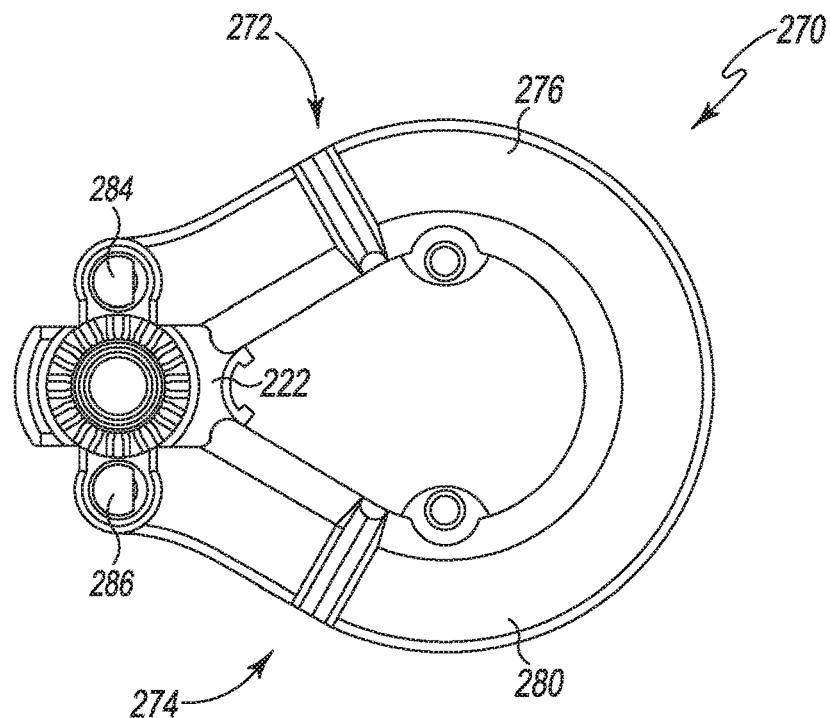
FIG. 36 is a top view of another alternative embodiment of a retraction system.
Figure 37:
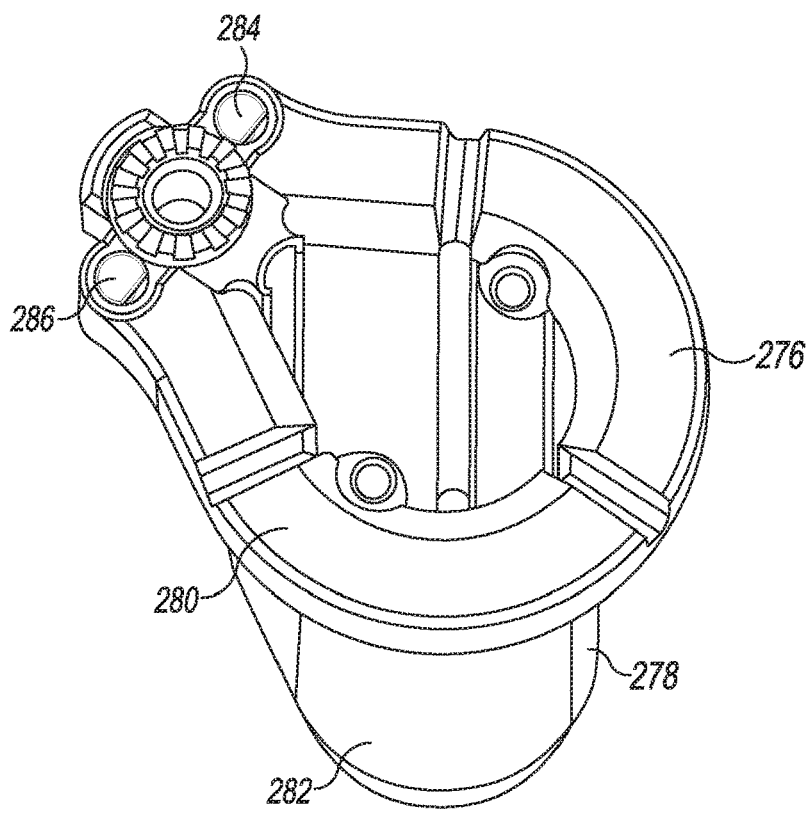
FIG. 37 is an isometric view of the retractor system of FIG. 36 according to one embodiment.
Figure 38:
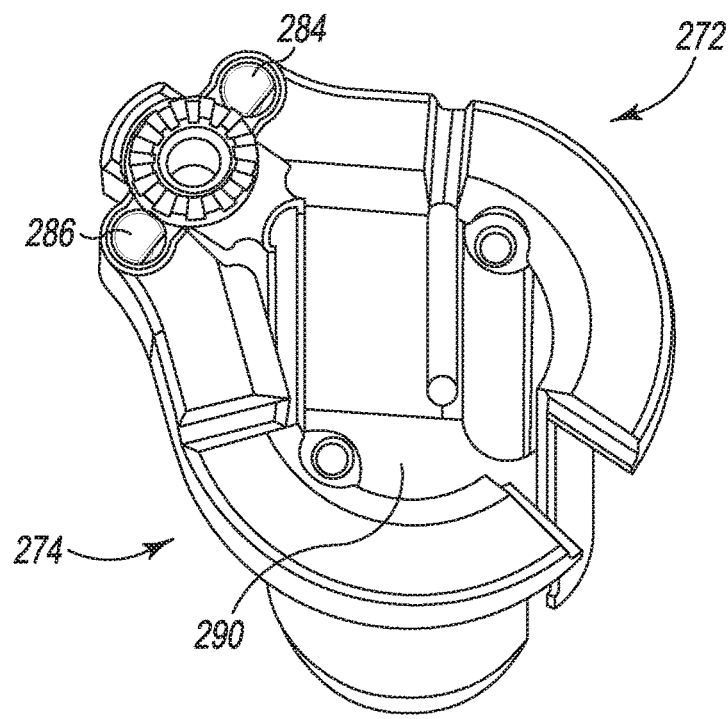
FIG. 38 is another isometric view the retractor system of FIG. 36 according to one embodiment.
Figure 39:
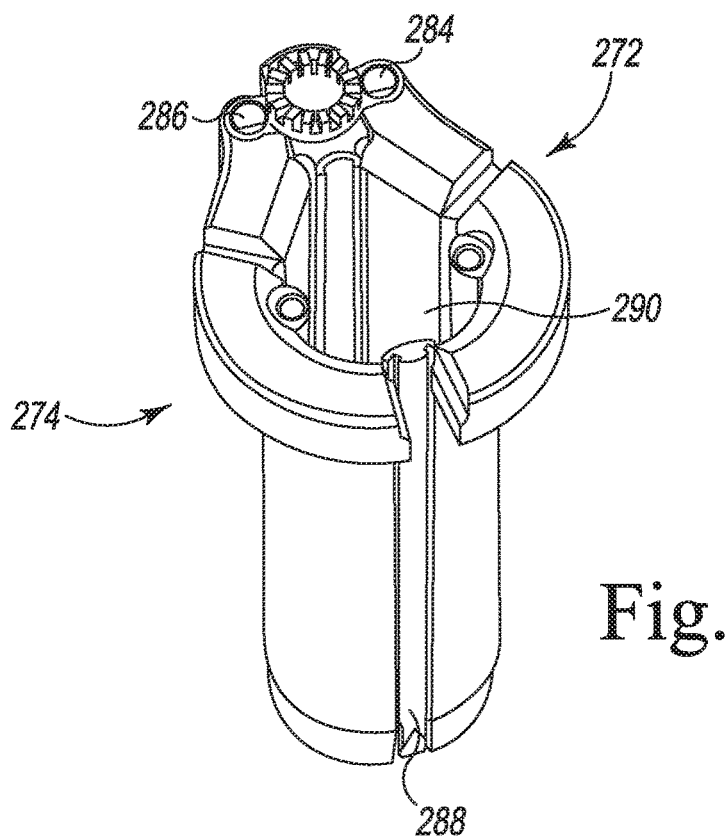
FIG. 39 is another isometric view the retractor system of FIG. 36 according to one embodiment.

Referring now to FIGS. 36-39, a retractor assembly 270 is shown according to another embodiment, and shares any or all of the features of retractor assembly 170, except that retractor assembly 170 provides a pivoting feature. Retractor assembly 270 includes a first portion 272 and a second portion 274 that collectively form a portion of the retractor wall. Retractor assembly 270 is coupled to dilator 222 in a similar fashion to retractor assembly 170. First and second portions 272, 274 are coupled to first and second hinge portions 284, 286, enabling relative pivotal movement of first and second portions 272, 274. FIGS. 36-37 show retractor assembly 270 in a closed position. FIGS. 38-39 show retractor assembly 270 in an open position, where the opposing end portions of first and second portions 272, 274 may be coupled using a spacer 288. Spacer 288 is slidably received by first and second portions 272, 274, and the size of spacer 288 may be varied to provide varying amounts of retraction. Thus, the size of working channel 249 can be increased by pivoting the first and second portions 272, 274 to an open position and inserting spacer 288.

In one embodiment, first portion 272 includes a first top portion 276 and a first retractor member 278, and second portion 274 includes a second top portion 280 and a second retractor member 282. First and second portions 272 and 274 are generally similar in size and shape, providing a symmetric working channel 290 to provide access to a surgical site.

While the invention has been illustrated and described in detail in the drawings and foregoing description, the same is to be considered as illustrative and not restrictive in character, it being understood that various embodiments have been shown and described and that all changes and modifications that come within the spirit of the invention are desired to be protected.

What is claimed is:

1. A system for providing access to a surgical site, comprising:
    a first dilator;
    a second dilator slidably couplable to a first side of the first dilator and including a first interface portion;
    a plurality of additional dilators slidably couplable to a second side of the first dilator in a nested manner, wherein each of the plurality of additional dilators includes a circular sidewall portion extending about a centerpoint, and wherein the centerpoint of each of the plurality of additional dilators is offset from the center point of adjacent ones of the plurality of additional dilators; and
    at least one retractor member including a second interface portion removably couplable to the first interface portion;
    wherein when the first interface portion is coupled to the second interface portion, and the second dilator and the plurality of additional dilators are coupled to the first dilator, the second dilator and the at least one retractor member form a retractor wall extending about the first dilator and the plurality of additional dilators.

2. The system of claim 1, wherein the first dilator and the plurality of additional dilators are removable relative to the retractor wall to provide a working channel defined by an interior of the retractor wall.

3. The system of claim 1, wherein an interior surface of the retractor wall and an exterior wall formed by the first dilator and the plurality of additional dilators have complimentary shapes.

4. The system of claim 1, wherein the first dilator includes a generally cylindrical elongated body defining a longitudinal axis, and wherein the plurality of additional dilators each provide an asymmetric dilation shape relative to the longitudinal axis of the cylindrical elongated body.

5. The system of claim 1, wherein the plurality of additional dilators includes:
    a first additional dilator slidably coupled to the first dilator and having a first cross-sectional area;
    a second additional dilator coupled to the first additional dilator and having a second cross-sectional area greater than the first cross-sectional area.

6. The system of claim 1, wherein the second dilator provides directional dilation in a first direction away from the first dilator and the plurality of additional dilators provide directional dilation in a second, opposite direction away from the first dilator;
    wherein a first one of the plurality of additional dilators extends only partially about the first dilator, and the other ones of the plurality of additional dilators each extends only partially about an adjacent one of the plurality of additional dilators.

7. The system of claim 1, wherein the first dilator is slidably couplable to the second dilator using a sliding dovetail interface.

8. The system of claim 1, wherein the at least one retractor member includes a first retractor member pivotally coupled to the second interface portion and a second retractor member pivotally coupled to the second interface portion such that an amount of distraction provided by the first and second retractor members is variable through pivoting of at least one of the first and second retractor members.

9. The system of claim 8, further comprising a spacer configured to be slidably received by the first and second retractor members and retain the first and second retractor members in a desired pivotal position.

10. The system of claim 8, wherein the first and second retractor members are mirror images.

11. A system for providing access to a surgical site, comprising:
    a first dilator;
    a second directional dilator including a first side slidably couplable to a first side of the first dilator and a second side including a first interface portion, wherein the second directional dilator extends about only a portion of the first dilator;
    a plurality of additional directional dilators slidably couplable to a second side of the first dilator in a nested manner, wherein a first additional dilator of the plurality of additional directional dilators extends about only a portion of the first dilator; and
    at least one retractor member including a second interface portion removably couplable to the first interface portion;
    wherein the at least one retractor member forms a retractor wall extending about the first dilator and the plurality of additional directional dilators.

12. The system of claim 11, wherein an interior surface defined by the second directional dilator and the at least one retractor member substantially conforms to an exterior surface formed by the first dilator and the plurality of additional directional dilators.

13. The system of claim 12, wherein the plurality of additional directional dilators includes:
    a second additional dilator coupled to the first additional dilator and having a second cross-sectional area greater than a first cross-sectional area of the first additional dilator.

14. The system of claim 11, wherein the at least one retractor member includes a first portion and a second portion configured to pivot relative to the first portion to vary a size of a working channel providing access to the surgical site.

* * * * *